(12) United States Patent
Momiyama et al.

(10) Patent No.: US 8,252,941 B2
(45) Date of Patent: Aug. 28, 2012

(54) PROCESS OF MAKING ALPHA-AMINOOXYKETONE/ALPHA-AMINOOXYALDEHYDE AND ALPHA-HYDROXYKETONE/ALPHA-HYDROXYALDEHYDE COMPOUNDS AND A PROCESS MAKING REACTION PRODUCTS FROM CYCLIC ALPHA, BETA-UNSATURATED KETONE SUBSTRATES AND NITROSO SUBSTRATES

(75) Inventors: Norie Momiyama, Sendai (JP); Hiromi Torii, Kariya (JP); Susumu Saito, Nagoya (JP); Hisashi Yamamoto, Chicago, IL (US); Yuhei Yamamoto, Tsukuba (JP)

(73) Assignee: Japan Science and Technology Agency, Saitama (JP)

( * ) Notice: Subject to any disclaimer, the term of this patent is extended or adjusted under 35 U.S.C. 154(b) by 288 days.

(21) Appl. No.: 12/578,836

(22) Filed: Oct. 14, 2009

(65) Prior Publication Data
US 2010/0099915 A1     Apr. 22, 2010

Related U.S. Application Data

(60) Division of application No. 11/506,590, filed on Aug. 18, 2006, now Pat. No. 7,872,123, which is a continuation-in-part of application No. PCT/US2005/005426, filed on Feb. 18, 2005.

(60) Provisional application No. 60/564,048, filed on Apr. 20, 2004.

(30) Foreign Application Priority Data

Feb. 20, 2004   (JP) .................................. 2004-44540

(51) Int. Cl.
C07D 257/04   (2006.01)
(52) U.S. Cl. ...................................................... 548/250
(58) Field of Classification Search .................... 548/250
See application file for complete search history.

(56) References Cited

PUBLICATIONS

Yujiro Hayashi, et al., Direct Proline Catalyzed Asymmetric α-Aminooxylation of Aldehydes, Tetrahedron Letters 44 (2003) 8293-8296.

Hiromi Torii, et al., Asymmetric Direct Aldol Reaction Assisted by Water and a Proline-Derived Tetrazole Catalyst, Angew. Chem. Int. Ed. (2004) vol. 43, 1983-1986.

Yuhei Yamamoto, et al., Enantioselective Tandem O-Nitroso Aldol/Michael Reaction, J. Am. Chem. Soc. (2004) vol. 126, 5962-5963.

Merino et al. Organocatalyzed Asymmetric alpha-Aminoxylation of aldehydes and ketones—An efficient access to enantiomerically pure alpha-hydroxycarbonyl compounds, diols, and even amino alcohols. 2004, Angewandte Chemie International Edition, 43, 2995-2997.

*Primary Examiner* — James O. Wilson
*Assistant Examiner* — Brian McDowell
(74) *Attorney, Agent, or Firm* — Frommer Lawrence & Haug LLP

(57) ABSTRACT

The present invention is directed to a process of making α-aminooxyketone and α-hydroxyketone compounds. The synthetic pathway generally involves reacting an aldehyde or ketone substrate and a nitroso substrate in the presence of a catalyst of the formula (IV):

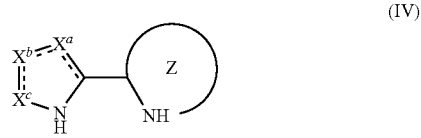

(IV)

wherein $X^a$—$X^c$ represent independently nitrogen, carbon, oxygen or sulfur and Z represents a 4 to 10-membered ring with or without a substituent and optionally a further step to convert the α-aminooxyketone compound formed to the α-hydroxyketone compound. The present invention results in α-aminooxyketone and α-hydroxyketone compounds with high enantioselectivity and high purity. The present invention is also directed to a catalytic asymmetric O-nitroso Aldol/Michael reaction. The substrates of this reaction are generally cyclic α,β-unsaturated ketone substrate and a nitroso substrate. This methodology generally involves reacting the cyclic α,β-unsaturated ketone substrate and the nitroso substrate in the presence of a proline-based catalyst, to provide a heterocyclic product.

4 Claims, 6 Drawing Sheets a)
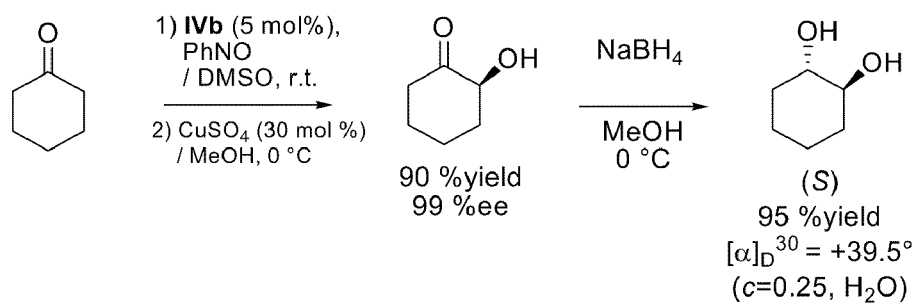
b)
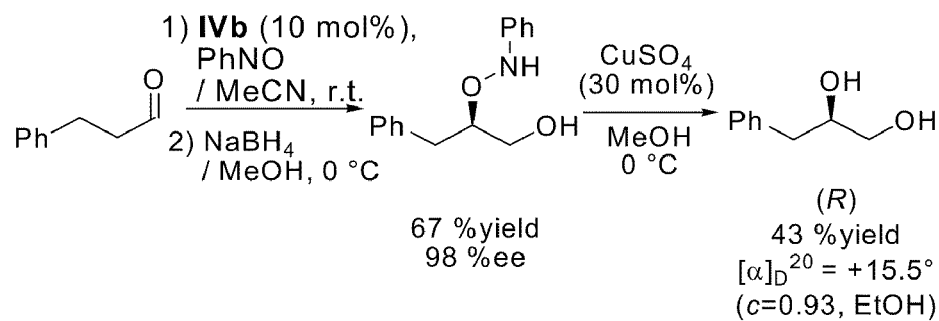
Figure 6. Process to determine absolute configuration of α-aminooxy compounds.

PROCESS OF MAKING ALPHA-AMINOOXYKETONE/ALPHA-AMINOOXYALDEHYDE AND ALPHA-HYDROXYKETONE/ALPHA-HYDROXYALDEHYDE COMPOUNDS AND A PROCESS MAKING REACTION PRODUCTS FROM CYCLIC ALPHA, BETA-UNSATURATED KETONE SUBSTRATES AND NITROSO SUBSTRATES

INCORPORATION BY REFERENCE

This application is a divisional of U.S. application Ser. No. 11/506,590, filed Aug. 18, 2006, now U.S. Pat. No. 7,872,123, which is a continuation in part (CIP) of PCT/US2005/005426 filed on Feb. 18, 2005, which claims the benefit of U.S. Provisional Application Serial No. 60/564,048 filed Apr. 20, 2004 and Japanese patent application Serial No. 2004-44540 filed Feb. 20, 2004.

The foregoing applications, and all documents cited therein or during their prosecution ("appln cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

STATEMENT OF FEDERALLY SPONSORED RESEARCH OR DEVELOPMENT

The subject matter of this application was in part funded by the National Institutes of Health (GM068433-01). The government may have certain rights in this invention.

FIELD OF THE INVENTION

This invention relates to a process of making α-aminoxyketones or α-hydroxyketones with high enantioselectivity and high purity and also describes the catalytic methods involved in the process of making α-aminoxyketones or α-hydroxyketones through a highly enantioselective O-nitroso aldol reaction between an aldehyde or ketone and a nitroso compound. The invention is also directed to a catalytic asymmetric O-nitroso Aldol/Michael reaction between a cyclic α,β-unsaturated ketone substrate and a nitroso compound. In both the enantioselective O-nitroso aldol and nitroso Aldol/Michael reactions, the chiral catalyst employed is derived from proline.

BACKGROUND OF THE INVENTION

α-Hydroxyketone compounds are found in natural products and frequently in the molecule framework of pharmaceutical compounds. They are synthetic equivalents for aldose compounds, e.g. pentoses and hexoses, and are very important synthetic building blocks which can lead to various physiologically active materials, medicines and intermediates in the synthesis of liquid crystalline materials.

α-Hydroxyketones can be obtained readily with high purity by asymmetric oxidation of carbonyl compounds. However, asymmetric oxidation of the α-position of the carbonyl group by the usual methods requires a two-step process. First, the preparation and isolation of an enolate, and second, the use of a relatively expensive oxygen-introducing reagent, which have the problem of low atom efficiency.

Other methods for direct preparation of chiral α-hydroxyketones without isolation of an enolate have been reported. These methods generally involve synthesizing enantioenriched α-aminooxyketones, which are precursors to α-hydroxyketones.

Previously disclosed were methods which used the amino acid proline as a catalyst and nitrosobenzene as an oxygen-introducing reagent to prepare α-aminooxyketones (see e.g. Brown, S. P., Brochu, M. P., Sinz, C. J. & MacMillan, D. W. C. (2003) *J. Am. Chem. Soc.* 125, 10808-10809; Zhong, G. (2003) *Angew. Chem. Int. Ed.* 42, 4247-4250; Hayashi, Y., Yamaguchi, J., Hibino, K. & Shoji, M. (2003) *Tetrahedron Lett.* 44, 8293-8296). However, many problems remain unsolved with this method, including a lack of catalytic efficiency (10 to 20 mol % catalyst is needed) and an inability to consistently reproduce results. Moreover, it is known that a second unwanted oxygen atom may be introduced via a side reaction with a second equivalent of nitrosobenzene.

Alternatively, it was reported that α-aminooxyketone could be obtained in high yield from an alkylsilyl ether and nitrosobenzene with alkylsilyl triflate as a Lewis Acid catalyst (see e.g. Momiyama, N., Yamamoto, H. (2002) *Angew. Chem. Int. Ed.* 41, 2986-2987) and also from an alkyltin enolate and nitrosobenzene with Ag-BINAP as a catalyst (see e.g. Momiyama, N., Yamamoto, H. (2003) *J. Am. Chem. Soc.* 125, 6038-6039).

Additionally, other methods have been disclosed to produce aldol products from the condensation reaction of carbonyl compounds by: (1) using a substrate with an ether or alcohol unit in the molecule with liquid $CO_2$, or supercritical $CO_2$ as a solvent (see e.g. Japanese Patent 2002-No. 284729); (2) running the reaction in water using boronic acid or a phase transfer catalyst or Brönsted acid (see e.g. Japanese Patent 2002-No. 275120); or (3) using a lanthanide triflate with a chiral crown ether (see e.g. Japanese Patent 2002-No. 200428).

Despite these methods for synthesizing α-aminooxyketone or α-hydroxyketone compounds, there is still a need in the art for a process which can produce α-aminooxyketone or α-hydroxyketone compounds with sufficient enantioselectivity, purity and/or reproducibility of results to enable these compounds to be suitable for use as synthetic building blocks or intermediates in a synthetic process.

One of the most intensely studied areas in chemical synthesis at present is the development of new enantioselective processes which are catalyzed by simple organic molecules. By using a proline-based chiral catalyst, we have discovered a reaction process which provides a method for the catalytic asymmetric synthesis of α-aminooxyketones via an O-nitroso Aldol reaction between an aldehyde or ketone and a nitroso compound. These compounds are easily converted into the synthetically important enantioenriched α-hydroxyketones.

Furthermore, we have developed a process for producing bicyclo ketones which contain nitrogen and oxygen heteroatoms via an asymmetric O-nitroso Aldol/Michael reaction between an α,β-unsaturated cyclic ketone with a nitroso compound. The product generated from this reaction is a Diels-Alder adduct that usually is formed through a typical Diels-Alder reaction. However, in the tandem O-Nitroso Aldol/Michael reactions described herein, the regiochemistry of the Diels-Alder adduct is opposite that of the normal nitroso Diels-Alder reaction. Owing to the ability to control both regiochemistry and stereochemistry, these catalytic asymmetric Aldol/Michael reactions provide novel routes to important or previously unaccessible heterocyclic compounds.

Citation or identification of any document in this application is not an admission that such document is available as prior art to the present invention.

SUMMARY OF THE INVENTION

The invention is based, in part, on applicants' development of a process of making α-aminoxyketones or α-hydroxyketones with high enantioselectivity and high purity and a method of preparing bicyclo ketones which contain nitrogen and oxygen heteroatoms through reacting an α,β-unsaturated cyclic ketone with a nitroso compound, where the regiochemistry of this product is opposite that of the normal nitroso Diels-Alder reaction.

The object of the invention provides a method to prepare α-aminooxyketone (which are precursors of α-hydroxyketones) and to develop new synthetic routes for making saccharide related compounds or glycosylation of compounds, especially those compounds with anti-cancer or anti-HIV effects.

Another object of the invention is to provide a method of preparing bicyclo ketones which contain nitrogen and oxygen heteroatoms when reacting an α,β-unsaturated cyclic ketone with a nitroso compound, where the regiochemistry of this product is opposite that of the normal nitroso Diels-Alder reaction.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

BRIEF DESCRIPTION OF THE DRAWINGS

FIG. 3. General reaction schemes for Examples 5a-12a.

FIGS. 6A and 6B. Process to determine absolute configuration of α-aminooxy compounds.

DETAILED DESCRIPTION

Figure 1:
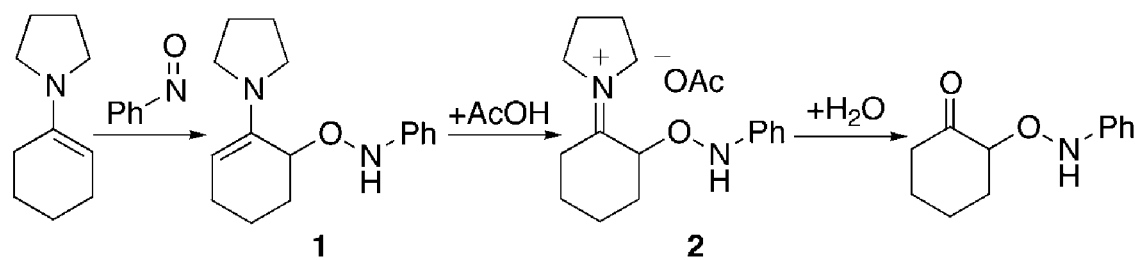
FIG. 1. Structure of intermediates in the reaction pathway of a pyrrolidine enamine and nitrosobenzene.

This invention provides a method to prepare α-aminooxyketone (which are precursors of α-hydroxyketones) which comprises reacting an aldehyde of formula (I) or ketone of formula (II):

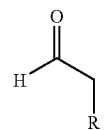
(I)

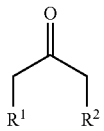
(II)

with a nitroso compound of formula (IIIa) or (IIIb):

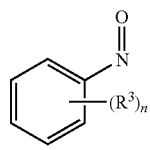
(IIIa)

(IIIb)

in the presence of a solvent and a catalyst of formula (IV):

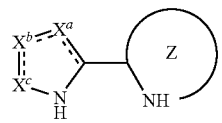
(IV)

wherein:

R, $R^1$ and $R^2$ independently represent either hydrogen; a substituted or unsubstituted alkyl group; a substituted or unsubstituted alkoxy group; a substituted or unsubstituted alkoxycarbonyl group; a substituted or unsubstituted aryl group; or $R^1$ and $R^2$ together form a cycloalkyl ring;

$R^3$ is each independently selected from the group consisting of:
  hydrogen, halogen, —$OR^5$, —$OC(O)R^5$, —CN, —$C(O)R^5$, —$CO_2R^5$, —$C(O)NR^5R^{5'}$, —$NO_2$, —$NR^5R^{5'}$, —$NRC(O)R^5$, —$NR^5CO_2R^{5'}$, —$NR^5S(O)_2R^{5'}$, —$SR^5$, —$S(O)R^5$, —$S(O)_2R^5$, —$S(O)_2NR^5R^{5'}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl; wherein
  each $R^5$ and $R^{5'}$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

n is an integer from 0-5;

$R^4$ is substituted or unsubstituted alkyl;

$X^a$, $X^b$ and $X^c$ independently represent oxygen; sulfur; substituted or unsubstituted nitrogen; or substituted or unsubstituted carbon with the bonds between $X^a$—$X^b$, $X^b$—$X^c$ and $X^a$—C (adjacent to nitrogen on pyrrolidine ring) being single or optionally double bonds;

Z represents a substituted or unsubstituted 4 to 10-membered ring (herein referred to as "the Z ring")which optionally contains up to three additional heteroatoms; and the bond between the two rings is in the (L) or optionally (D) configuration.

Another embodiment of the invention is where:

R, $R^1$ and $R^2$ independently represent either hydrogen; a substituted or unsubstituted
  $C_1$-$C_8$ alkyl group; a substituted or unsubstituted $C_1$-$C_8$ alkoxy group; a substituted or unsubstituted $C_1$-$C_8$ alkoxycarbonyl group; a substituted or unsubstituted aryl group, wherein the groups when substituted are substituted by the group consisting of of hydrogen, halogen, —$OR^4$, —$OC(O)R^4$, —CN, —$C(O)R^4$, —$CO_2R^4$, —$C(O)NR^4R^5$, —$NO_2$, —$NR^4R^5$, —$NRC(O)R^4$, —$NR^4CO_2R^5$, —$NR^4S(O)_2R^5$, —$SR^4$, —$S(O)R^4$, —$S(O)_2R^4$, —$S(O)_2NR^4R^5$, $C_{1-8}$ alkyl, $C_{3-8}$ cycloalkyl, $C_{6-10}$ aryl, 5- to 10-membered heteroaryl, and 3- to 10-membered heterocyclyl; or $R^1$ and $R^2$ together form a $C_3$-$C_8$ cycloalkyl ring;

$R^3$ is each independently selected from the group consisting of:
  hydrogen, halogen, —$OR^5$, —$OC(O)R^5$, —CN, —$C(O)R^5$, —$CO_2R^5$, —$C(O)NR^5R^{5'}$, —$NO_2$, —$NR^5R^{5'}$, —$NRC(O)R^5$, —$NR^5CO_2R^{5'}$, —$NR^5S(O)_2R^{5'}$, —$SR^5$, —$S(O)R^5$, —$S(O)_2R^5$, —$S(O)_2NR^5R^{5'}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl; wherein
  each $R^5$ and $R^{5'}$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

$R^4$ is a substituted or unsubstituted $C_1$-$C_8$ alkyl, wherein when substituted are substituted by the group consisting of halogen, —$OR^5$, —$OC(O)R^5$, —CN, —$C(O)R^5$, —$CO_2R^5$, —$C(O)NR^5R^{5'}$, —$NO_2$, —$NR^5R^{5'}$, —$NRC(O)R^5$, —$NR^5CO_2R^{5'}$, —$NR^5S(O)_2R^{5'}$, —$SR^5$, —$S(O)R^5$, —$S(O)_2R^5$, —$S(O)_2NR^5R^{5'}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl; wherein
  each $R^5$ and $R^{5'}$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

n is an integer from 0-3;

$X^a$, $X^b$ and $X^c$ independently represent oxygen; sulfur; substituted or unsubstituted nitrogen; or substituted or unsubstituted carbon with the bonds between $X^a$—$X^b$, $X^b$—$X^b$ and $X^a$—C (adjacent to nitrogen on pyrrolidine ring) being single or optionally double bonds;

Z represents a substituted or unsubstituted 4 to 10-membered ring which optionally contain up to three additional heteroatoms; and the bond between the two rings is in the (L) or optionally (D) configuration.

In another embodiment of the invention, advantageous alkyl group for $R^1$ and $R^2$ include linear or cyclic alkyl groups with 1-30 carbons which include but are not limited to methyl, ethyl, n-propyl, n-butyl, n-pentyl, n-hexyl, n-heptyl, n-octyl, n-nonyl, n-decyl, cyclobutyl, cyclopentyl, cyclohexyl, cycloheptyl, cyclooctyl, cyclononyl, or cyclodecyl.

In another embodiment of the invention, advantageous alkoxy group, alkoxycarbonyl group and aryl group for R, $R^1$ and $R^2$ are alkoxy groups with 1-30 carbons which include but are not limited to methoxy, ethoxy, n-propoxy, n-butoxy, n-pentyloxy, n-hexyloxy, cyclohexyloxy, phenyloxy; alkoxycarbonyl group with 1-30 carbons which include but are not limited to methoxy-carbonyl, ethoxy-carbonyl, butoxy-carbonyl, pentyloxy-carbonyl and the aryl group with 6~30 carbon atoms which include but are not limited to phenyl, 1-naphtyl, 2-naphthyl, 1-anthryl, 2-anthryl, 9-anthryl, 1-phenanthryl, 2-phenanthryl, benzyl, or phenyl.

In another embodiment of the invention, advantageous alkyl groups, alkoxy groups, alkoxy-carbonyl groups and aryl groups for R, $R^1$ and $R^2$ include but are not limited to methyl, ethyl, n-propyl, n-butyl, cyclohexyl, cycloheptyl, as a alkyl group; phenyl, 1-naphthyl, 2-naphthyl, 1-anthryl, 1-phenanthryl, benzyl as an aryl group; and advantageous substituents include but are not limited to F, Cl, or Br as a halogen group; methoxy, ethoxy, propoxy, butoxy as an alkoxy group; or hydroxyl, carboxyl, acyl, amino, thio, or nitro group.

In another embodiment of the invention, advantageous ring systems for $R^1$ and $R^2$ include but are not limited to cyclopentane, cyclohexane, cycloheptane, cyclooctane, cyclononane, cyclodecane as an alkyl group; or benzene, naphthalene, anthracene, as an aromatic; or pyridine, pyrrolidine, piperidine, furan, pyran, tetrahydrofuran, tetrahydropyran as heteroaromatics.

In another embodiment of the invention, advantageous aldehydes of formula (I) include but are not limited to acetaldehyde, propylaldehyde, butylaldehyde, isobutylaldehyde, valeraldehyde, isovaleraldehyde, caproaldehyde, heptaldehyde, caprylic aldehyde, caprylic aldehyde, undecylaldehyde, lauraldehyde, tridecylaldehyde, pentadecylaldehyde, palmitic aldehyde, stearic aldehyde, squaric aldehyde.

In another embodiment of the invention, advantageous ketones of formula (II) include but are not limited to acetone, ethylmethylketone, propylmethylketone, isopropylmethylketone, butylmethylketone, diethylketone, diisopropylketone, 2-undecanone, fluoroacetone, chloroacetone, 2,4-pentadione, cyclobutanone, cyclopentanone, 2-methylcyclohexanone, cyclodecanone, 2-norbornanone, 2-adamantanone, tetrahydropyrane-4-one, spiro[4,5]-1,4-dioxy-decane-8-one, 1-benzylcarbonylpyperidine-4-one, 1-indanone, 2-indanone, α-tetralone, β-tetralone, 7-methoxy-2-tetralone, acetophenone, propiophenone, benzylphenone, dibenzylketone, 3,4-dimethylacetophenone, 2-acetophenone, 2-choroloacetophenone.

In an advantageous embodiment of the invention, the aldehyde (formula (I)) or ketone (formula (II)) are selected from the group consisting of:

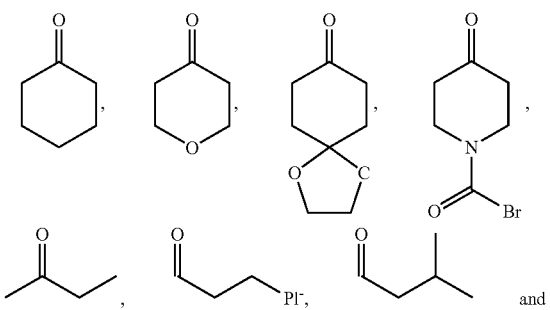

-continued

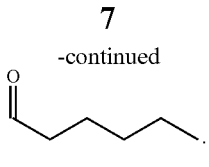

In another embodiment of the invention, advantageous nitroso compounds of formula (III) include but are not limited to alkyl nitroso compounds wherein nitroso substitution is at the tertiary carbon, e.g. 2-nitroso-isobutane, 2-nitroso-2-methylpentane. Advantageous substituted aryl nitroso compounds include but are not limited to substituted nitrosobenzenes or 2-nitrosonaphthalene. Advantageous substituents for alkylnitroso catalysts include but are not limited to methyl, ethyl, propyl, isopropyl, n-butyl, isobutyl, s-butyl, t-butyl, alkoxy groups like methoxy, ethoxy, n-propoxy, isopropoxy, n-butoxy, s-butoxy, isobutoxy, t-butoxy, phenoxy, benzyloxy, phenethyloxy, or halogens like F, Cl, Br, I. Advantageous substituents for nitrosobenzene include but are not limited to o-nitrosotoluene, m-nitrosotoluene, p-nitrosotoluene, 3,5-dimethylnitrosobenzene, o-nitrosoethylbenzene, o-nitrosostyrene, o-nitrosoanisole, p-nitrosoanisole, o-nitrosophenol, m-nitrosophenol, o-fluoronitrosobenzene, m-fluoronitrosobenzene, p-fluoronitrosobenzene, o-chrolonitrosobenzene, m-chrolonitrosobenzene, p-chloronitrosobenzene, o-bromonitrosobenzene, m-bromonitrosobenzene, p-bromonitrosobenzene.

In an advantageous embodiment of the invention, the nitroso compound is Ph-N=O.

In another embodiment of the invention, in the catalyst of formula (IV), the 5-membered ring bonded to the Z-ring is an aromatic ring. The 5-membered aromatic heterocyclic ring includes but is not limited to tetrazole, 1,2,3-triazole, 1,2,4-triazole, pyrazole, pyrazoline, imidazole, imidazoline, thiotriazoline and oxatriazoline. Advantageously, the five-membered ring is a tetrazole as disclosed in formula (IVa) below:

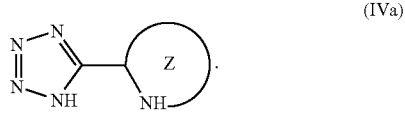

(IVa)

The 5-10 membered heterocycle (Z-ring) bonded to the triazole ring in formula IVa includes but is not limited to pyrrolidine, piperidine, hexamethyleneimine, heptamethyleneimine, oxazoline, oxazole, and substituents for these heterocycles which include but are not limited to alkyl groups like methyl, ethyl, n-propyl, isopropyl, n-butyl, isobutyl, sec-butyl, or t-butyl groups, or alkoxy groups like methoxy or ethoxy. Smaller substituents are advantageous since a bulky ones would lower the yield of the process. The stereocenter adjacent to the nitrogen on the Z-ring is in the (L) or optionally (D) configuration.

Advantageously, the catalyst of formula (IV) includes but is not limited to 5-(2'-pyrrolidinyl)-1H-1,2,3,4-tetrazole, 5-(4H, 5H-2'-oxazolyl)-1H-1,2,3,4-tetrazole, 5-(2'-piperidinyl)-1H-1,2,3,4-tetrazole, 5-benzo[c]-2'-piperidinyl-1H-1,2,3,4-tetrazole, 5-2'-pyrolidinyl-1H-1,2,3-triazole, 5-2'-pyrolidinyl-1H-1,2,4-triazole, 2-2'-pyrolidinyl-1H-imidazole, 5-2'-pyrolidinyl-1H-imidazole, 5-2'-pyrolidinyl-1H, 4H, 5H-1,2,3,4-thiotriazoline, 5-2'pyrolidinyl-4H, 5H-pyrazoline. Most advantageous is 5-(2'-pyrrolidinyl)-1H-1,2,3,4-tetrazole as shown in structure (IVb):

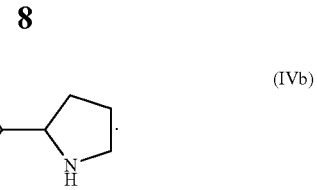

(IVb)

The configuration of the stereogenic carbon adjacent to the nitrogen on the pyrolidine ring is the (L) or optionally (D) configuration.

In another embodiment of the invention, the enantioselectivity of the α-aminooxyketones and α-aminooxyaldehydes compounds produced by the process of the invention is greater than about 90% ee. Advantageously, enantioselectivity is greater than about 95% ee. More advantageously, enantioselectivity is greater than 99% ee.

In another embodiment of the invention, the purity of the α-aminooxyketones and α-aminooxyaldehydes compounds produced by the process of the invention is greater than about 90%. Advantageously, purity is greater than about 95%. More advantageously, purity is greater than 99%.

In another embodiment of the invention, the product yield of the α-aminooxyketones and α-aminooxyaldehydes compounds produced by the process of the invention is greater than about 80%. Advantageously, product yield is greater than about 85%. More advantageously, product yield is greater than 90%.

In another embodiment of the invention, the amount of catalyst of formula (IV) used in the process of the invention is less than about 10 mol % but greater than 0 mol %. Advantageously, the amount of catalyst of formula (IV) is the range of from about 2 mol % to about 5 mol %. More advantageously, the amount of catalyst of formula (IV) is about 5 mol %.

In another embodiment of the invention, the molar equivalent ratio of aldehyde (compound of formula (I)) or ketone (compound of formula (II)) starting material to nitroso compound of formula (IIIa) or (IIIb) is between about 10:1 to about 1:2. Advantageously, the molar equivalent ratio of aldehyde (compound of formula (I)) or ketone (compound of formula (II)) starting material to nitroso compound of formula (IIIa) or (IIIb) is between about 5:1 to about 1:1. More advantageously, the molar equivalent ratio of aldehyde (compound of formula (I)) or ketone (compound of formula (II)) starting material to nitroso compound of formula (IIIa) or (IIIb) is about 3:1.

In another embodiment of the invention, the solvent used in the process of the invention may be any solvent which facilitates the reaction of the aldehyde or ketone starting material and the nitroso compound in the presence of the catalyst of formula (IV). Advantageous examples include but are not limited to dimethylsulfoxide (DMSO), acetonitrile (MeCN), pyridine (Py) and dimethylformamide (DMF).

In another embodiment of the invention, corresponding α-hydroxyketones based on the α-aminooxyketones and aldehydes of the invention may be synthesized by treatment of an α-aminooxyketones or aldehydes with $CuSO_4$ to in solution using known methods. Possible solvents include alcohols like methanol and ethanol. The reaction temperature can be about 0° C.-25° C., and the reaction time can be about 3-10 hours.

The invention to synthesize α-aminooxyketones comprises reacting a carbonyl compound and a nitroso compound in the presence of the catalyst which is shown in general structure (IV) or preferably tetrazole derivative (IVa or IVb). The amount of nitroso compound could be in a range of 2-4 equivalents and is preferably 2.5-3.5 equivalents versus the carbonyl compound and the amount of catalyst which is shown in scheme (III) could be 1-10 mol % and preferably 2-20 mol %. The solvent could be water, chloroalkane like dichloromethane, chloroform, dichloroethane, chlorobenzene, hydrocarbon aromatics like benzene, toluene, xylene, aliphatic hydrocarbons like cyclohexane, n-hexane, n-heptane, esters like ethylacetate, nitriles like acetonitrile or dimethylsulfoxide and preferably dimethylsulfoxide or acetonitrile. The amount of the solvent could be 15-30 volumes but the reaction can be performed without solvent. The reaction temperature could be 0-50° C. and preferably 20-30° C. but the reaction can be performed at room temperature. The reaction time can be 30 minutes to 3 hours, and for example the reaction can be performed in open air with stirring for 1 hour. The reaction is very mild and furthermore, water will not inhibit the reaction, so there is no need for dehydrating the starting material and catalyst and the reaction is easy to control. After the reaction is complete, the product can be extracted with ethyl acetate and then dried and purified through known methods.

The reaction between the proline-derived catalysts used in the present invention and an aldehyde or ketone is suspected to yield an enanmine intermediate. We postulated that the O-nitroso Aldol reactions of the present invention also involve the intermediacy of an enamine. To test this hypothesis, a simple enamine derived from pyrrolidine and cyclohexane was reacted with nitrosobenzene. The schematic of this reaction is displayed in FIG. 1. Reaction of nitrosobenzene with pyrrolidine enamine in benzene at 0° C. generated a new intermediate 1, which was converted to the second intermediate 2 by the exposure of acetic acid. The intermediate 2 was able to be transformed to the aminooxy ketone after usual work-up (FIG. 1). Various solvents and temperature combination were examined for this transformation, and DMSO emerged as the most suitable solvent to afford aminooxy ketone without production of azoxy dimmer byproduct. $^1$H NMR study in DMSO-$d_6$ revealed a downfield shift of enamine olefin proton (J=3.9 Hz) from δ4.1 to 4.4 ppm, one proton broad singlet at δ8.2 ppm due to the aminooxy NH, and one proton triplet (J=4.5 Hz) at pyrrolidine α-position at δ4.3 ppm, which indicate the formation of the intermediate 1 (32). After treatment with acetic acid, complete conversion to a single new species is observed. This is assigned as the iminium salt 2 (33, 34); the significant downfield shift from δ4.3 to 5.3 ppm (α-proton of iminium group) and disappearance of δ4.4 ppm triplet (35). After work-up, the iminium salt 2 can be hydrized to α-aminooxy ketone.

Figure 2:
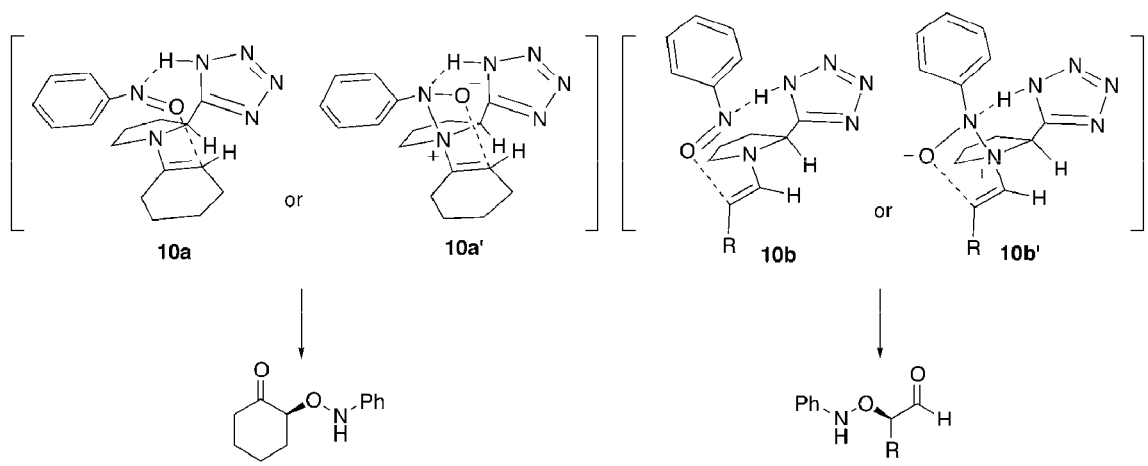
FIG. 2 Proposed transition states for enantioselective reactions between ketones (left) or aldehydes (right) with nitrosobenzene.

Interestingly, in the O-nitroso aldol reactions, aldehyde substrates afford products with the opposite configuration of those of ketone substrates. This observation suggests the possibility of different transition states depending on the choice of starting carbonyl compounds. Proposed transition states that account for this observation are displayed in FIG. 2. A possible explanation that accounts for the observed stereochemistry is that the bulkier ketone substrate will be forced to adopt a conformation which limits steric interactions in the transition state. The less bulky aldehyde will be freer to adopt a conformation which maximizes the electronic interactions in the transition state. While not wishing to be bound by theory, the reaction of nitrosobenzene may proceed from the same side of tetrazole (or carboxylic acid) by either direct activation of nitrosobenzene by acidic proton (10a, 10b) or indirect route via amine-nitrosobenzene complexation followed by rearrangement (10a', 10b'). The proposed transition states for the O-nitroso aldol reaction of ketones (left) and aldehydes (right) is shown below:

The invention also provides a method for performing highly enantioselective O-nitroso Aldol/Michael reactions between α,β-unsaturated ketones and nitroso substrates catalyzed by a proline-derived compound. More specifically, the catalytic nitroso aldol/Michael reaction provides a means of generating enantioenriched bicyclo ketones containing a nitrogen and an oxygen atom. The methodology affords a product bicyclo ketone which is not normally available from running a classical hetero Diels-Alder reaction.

The process of making reaction products from cyclic α,β-unsaturated ketone substrates and nitroso substrates (also referred to as a catalytic asymmetric O-nitroso Aldol/Michael Reaction) may be represented as follows:

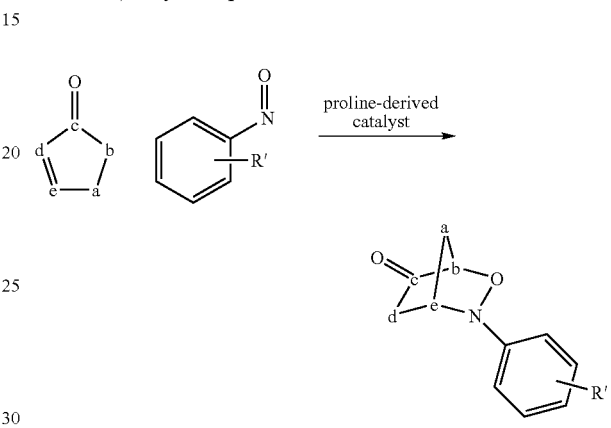

This reaction provides a method for the catalytic asymmetric synthesis of a heterocyclic product that has the opposite regiochemistry of this product formed in a hetero Diels-Alder reaction. The hetero-Diels-Alder product is shown below:

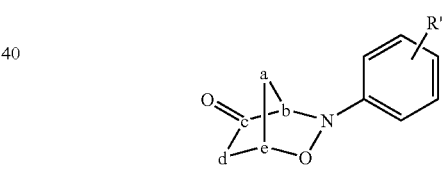

In one embodiment, the cyclic α,β-unsaturated ketone substrate may be represented by formulae (V), (VI), (VII), (VIII), (IX), or (X):

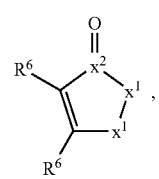

V

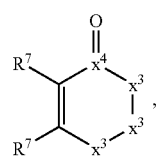

VI

-continued

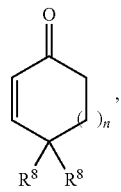
VII

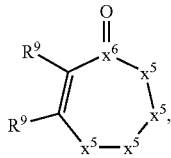
VIII

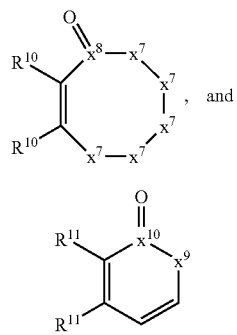
IX, and

X

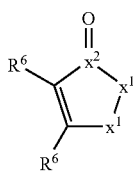

where $R^6$, $R^7$, $R^8$, $R^9$, $R^{10}$, $R^{11}$, $X^1$, $X^2$, $X^3$, $X^4$, $X^5$, $X^6$, $X^7$, $X^8$, $X^9$, $X^{10}$ and n are as defined below.

In one embodiment, the cyclic α,β-unsaturated ketone substrate may have a structure (V):

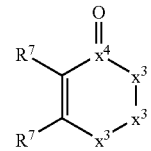
V where:
each $R^6$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;
each $X^1$ may independently represent —$CR^{12}R^{13}$—, —$NR^{12}$—, —O—, or —S—;
$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;
each $R^{12}$ and $R^{13}$, together with the atom to which they are attached, may form a 5-, 6- or 7-membered heterocyclic ring; and $X^2$ may represent —C— or —S—;
each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the cyclic α,β-unsaturated ketone substrate may have a structure (V) wherein:
each $R^6$ may represent a substituent independently selected from the group consisting of hydrogen, $C_{1-8}$ alkyl, $C_6$ aryl and a 5-membered heterocyclyl,
each $X^1$ may independently represent —$CR^{12}R^{13}$—;
$R^{12}$ and $R^{13}$ may represent a substituent independently selected from the group consisting of hydrogen, $C_{1-8}$ alkyl, $C_6$ aryl and a 5-membered heterocyclyl,
$X^2$ may represent —C—.

In one embodiment, the cyclic α,β-unsaturated ketone substrate may have a structure (VI):

VI where:
each $R^7$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;
each $X^3$ may independently represent —$CR^{12}R^{13}$—, —$NR^{12}$—, —O—, or —S—;
$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;
each $R^{12}$ and $R^{13}$, together with the atom to which they are attached, may form a 5-, 6- or 7-membered heterocyclic ring; and
$X^4$ may represent —C— or —S—;
each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the cyclic α,β-unsaturated ketone substrate may have a structure (VI) wherein:
each $R^7$ may represent a substituent independently selected from the group consisting of hydrogen, $C_{1-8}$ alkyl, $C_6$ aryl and a 5-membered heterocyclyl,
each $X^3$ may independently represent —$CR^{12}R^{13}$—;
$R^{12}$ and $R^{13}$ may represent a substituent independently selected from the group consisting of hydrogen, $C_{1-8}$ alkyl, $C_6$ aryl and a 5-membered heterocyclyl,
$X^4$ may represent —C—.

In one embodiment, the cyclic α,β-unsaturated ketone substrate may have a structure (VII):

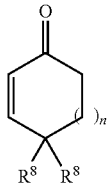

VII where,
each $R^8$ may independently represent a substituent selected from the group consisting of hydrogen, halogen, —$OR^c$, —$OC(O)R^c$, —CN, —$C(O)R^c$, —$CO_2R^c$, —$C(O)NR^cR^d$, —$NO_2$, —$NR^cR^d$, —$NR^cC(O)R^d$, —$NR^cCO_2R^d$, —$NR^cS(O)_2R^d$, —$SR^c$, —$S(O)R^c$, —$S(O)_2R^c$, —$S(O)_2NR^cR^d$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;
n may be 0, 1, 2, or 3; and
each $R^c$ and $R^d$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the cyclic α,β-unsaturated ketone substrate may have a structure (VII) wherein:
each $R^8$ may represent a substituent independently selected from the group consisting of hydrogen, $C_{1-8}$ alkyl, $C_6$ aryl and 5-membered heterocyclyl; and
n is 0 or 1.

In one embodiment, the cyclic α,β-unsaturated ketone substrate may have a structure (VIII):

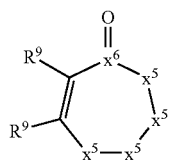

VIII where:
each $R^9$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;
each $X^5$ may independently represent —$CR^{12}R^{13}$—, —$NR^{12}$—, —O—, or —S—;
$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

each $R^{12}$ and $R^{13}$, together with the atom to which they are attached, may form a 5-, 6- or 7-membered heterocyclic ring; and
$X^6$ may represent —C— or —S—;
each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the cyclic α,β-unsaturated ketone substrate may have a structure (VIII) wherein:
each $R^9$ may represent a substituent independently selected from the group consisting of hydrogen, $C_{1-8}$ alkyl, $C_6$ aryl and a 5-membered heterocyclyl,
each $X^5$ may independently represent —$CR^{12}R^{13}$—;
$R^{12}$ and $R^{13}$ may represent a substituent independently selected from the group consisting of hydrogen, $C_{1-8}$ alkyl, $C_6$ aryl and a 5-membered heterocyclyl,
$X^6$ may represent —C—.

In one embodiment, the cyclic α,β-unsaturated ketone substrate may have a structure (IX):

IX where:
each $R^{10}$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;
each $X^7$ may independently represent —$CR^{12}R^{13}$—, —$NR^{12}$—, —O—, or —S—;
$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;
each $R^{12}$ and $R^{13}$, together with the atom to which they are attached, may form a 5-, 6- or 7-membered heterocyclic ring; and
$X^8$ may represent —C— or —S—;
each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the cyclic α,β-unsaturated ketone substrate may have a structure (IX) wherein:
each $R^{10}$ may represent a substituent independently selected from the group consisting of hydrogen, $C_{1-8}$ alkyl, $C_6$ aryl and a 5-membered heterocyclyl,
each $X^7$ may independently represent —$CR^{12}R^{13}$—;
$R^{12}$ and $R^{13}$ may represent a substituent independently selected from the group consisting of hydrogen, $C_{1-8}$ alkyl, $C_6$ aryl and a 5-membered heterocyclyl, $X^8$ may represent —C—.

In one embodiment, the cyclic α,β-unsaturated ketone substrate may have a structure (X):

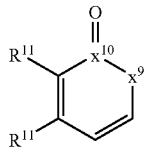

where:
each $R^{11}$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

$X^9$ may represent —$CR^{12}R^{13}$—, —$NR^{12}$—, —O—, or —S—;

$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

each $R^{12}$ and $R^{13}$, together with the atom to which they are attached, may form a 5-, 6- or 7-membered heterocyclic ring; and $X^{10}$ may represent —C— or —S—;

each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the cyclic α,β-unsaturated ketone substrate may have a structure (X) wherein:

each $R^{11}$ may represent a substituent independently selected from the group consisting of hydrogen, $C_{1-8}$ alkyl, $C_6$ aryl and a 5-membered heterocyclyl, each $X^9$ may independently represent —$CR^{12}R^{13}$—;

$R^{12}$ and $R^{13}$ may represent a substituent independently selected from the group consisting of hydrogen, $C_{1-8}$ alkyl, $C_6$ aryl and a 5-membered heterocyclyl, $X^{10}$ may represent —C—.

In one embodiment, the cyclic α,β-unsaturated ketone substrate may be selected from the group consisting of:

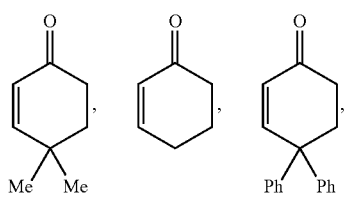

-continued

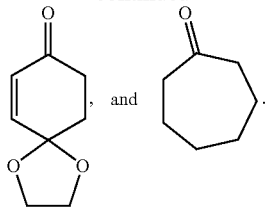

In one embodiment, the nitroso substrate may be represented by the structure XI.

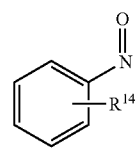

where:
$R^{14}$ may represent 1 to 5 substituents each independently selected from the group consisting of hydrogen, halogen, —$OR^{iii}$, —$OC(O)R^{iii}$, —CN, —$C(O)R^{iii}$, —$CO_2R^{iii}$, —$C(O)NR^{iii}R^{iv}$, —$NO_2$, —$NR^{iii}R^{iv}$, —$NR^{iii}C(O)R^{iv}$, —$NR^{iii}CO_2R^{iv}$, —$NR^{iii}S(O)_2R^{iv}$, —$SR^{iii}$, —$S(O)R^{iii}$, —$S(O)_2R^{iii}$, —$S(O)_2NR^{iii}R^{iv}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

each $R^{iii}$ and $R^{iv}$ may be independently selected from the group consisting of $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment of the invention, the nitroso substrate may be represented by the structure (XI) wherein:

$R^{14}$ may represent 1 to 5 substituents each independently selected from the group consisting of hydrogen, halogen and $C_{1-8}$ alkyl.

In another embodiment of the invention, the nitroso substrate may be selected from the group consisting of:

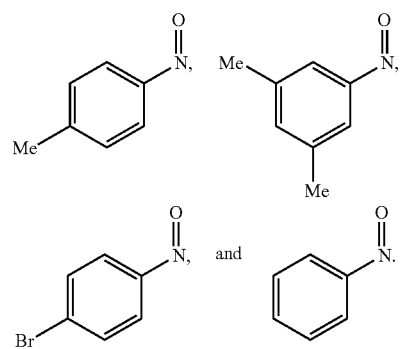

In one embodiment, the proline-based catalyst used in the O-nitroso Aldol/Michael reaction may be represented by the following structure (XII), wherein the stereocenter on the pyrrolidine ring (alpha to the nitrogen) is in the (L) or optionally (D) configuration.

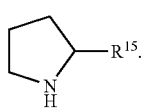

The R[15] substituent may be selected from the group consisting of:

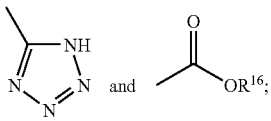

The R[16] may be a substituent selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In an advantageous embodiment of the invention, the proline-base catalyst may be selected from the group consisting of:

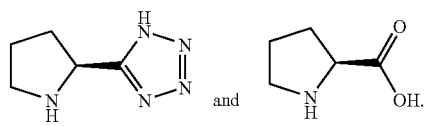

In another embodiment, the enantioselective O-nitroso Aldol/Michael reaction is carried out in the presence of a catalyst with the following formula:

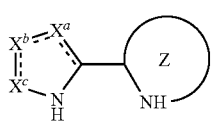

where:

$X^a$, $X^b$ and $X^c$ independently represent oxygen; sulfur; substituted or unsubstituted nitrogen; or substituted or unsubstituted carbon with the bonds between $X^a$—$X^b$, $X^b$—$X^o$ and $X^a$—C (alpha to nitrogen) being single or optionally double bonds;

Z represents a substituted or unsubstituted 4 to 10-membered ring which optionally contain up to three additional heteroatoms; and the bond between the two rings is in the (L) or optionally (D) configuration.

In another embodiment of the invention, in the catalyst of formula (IV), the 5-membered ring bonded to the Z-ring is an aromatic ring. The 5-membered aromatic heterocyclic ring includes but is not limited to tetrazole, 1,2,3-triazole, 1,2,4-triazole, pyrazole, pyrazoline, imidazole, imidazoline, thiotriazoline and oxatriazoline. Advantageously, the five-membered ring is a tetrazole as disclosed in formula (IVa) below:

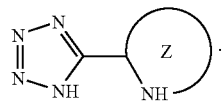

The 5-10 membered heterocycle (Z-ring) bonded to the triazole ring in formula IVa includes but is not limited to pyrrolidine, piperidine, hexamethyleneimine, heptamethyleneimine, oxazoline, oxazole, and substituents for these heterocycles which include but are not limited to alkyl groups like methyl, ethyl, n-propyl, isopropyl, n-butyl, isobutyl, sec-butyl, or t-butyl groups, or alkoxy groups like methoxy or ethoxy. Smaller substituents are advantageous since a bulky ones would lower the yield of the process. The stereocenter alpha to the nitrogen on the Z-ring is in the (L) or optionally (D) configuration.

Advantageously, the catalyst of formula (IV) includes but is not limited to 5-(2'-pyrrolidinyl)-1H-1,2,3,4-tetrazole, 5-(4H, 5H-2'-oxazolyl)-1H-1,2,3,4-tetrazole, 5-(2'-piperidinyl)-1H-1,2,3,4-tetrazole, 5-benzo[c]-2'-piperidinyl-1H-1,2, 3,4-tetrazole, 5-2'-pyrolidinyl-1H-1,2,3-triazole, 5-2'-pyrolidinyl1H-1,2,4-triazole, 2-2'-pyrolidinyl-1H-imidazole, 5-2'-pyrolidinyl-1H-imidazole, 5-2'-pyrolidinyl-1H, 4H, 5H-1,2,3,4-thiotriazoline, 5-2'pyrolidinyl-4H, 5H-pyrazoline. Most advantageous is 5-(2'-pyrrolidinyl)-1H-1,2,3,4-tetrazole as shown in structure (IVb):

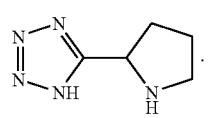

The configuration of the stereogenic carbon alpha to the nitrogen on the pyrolidine ring is the (L) or optionally (D) configuration.

The proline-based catalysts of the invention may be obtained via the methods and processes described above in the "Detailed Description for the Process of Making α-aminooxyketone/α-aminooxyaldehyde and α-hydroxyketone/α-hydroxyaldehyde" and "Examples for the Process of Making α-aminooxyketone/α-aminooxyaldehyde and α-hydroxyketone/α-hydroxyaldehyde" which is incorporated herein by reference.

In one embodiment, the heterocyclic product formed by the enantioselective O-nitroso/aldol reaction between the compound of formula V and the compound of formula XI is represented by the following structure (XIII):

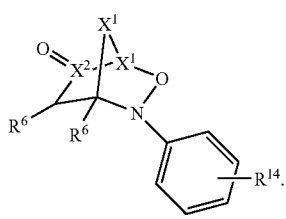

where:

each $R^6$ may represent a substituent independently selected from the group consisting of hydrogen, halogen, —$OR^i$, —$OC(O)R^i$, —CN, —$C(O)R^i$, —$CO_2R^i$, —$C(O)NR^i$ $R^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $X^1$ may independently represent —$CR^{12}R^{13}$—, —$NR^{12}$—, —O—, or —S—;

$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, cycloalkyl, $C_{6-10}$ aryl, 5- to 10-membered heteroaryl, and 3- to 10-membered heterocyclyl;

each $R^{12}$ and $R^{13}$, together with the atom to which they are attached, may form a 5-, 6- or 7-membered heterocyclic ring; and $X^2$ may represent —C— or —S—;

each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

$R^{14}$ may represent 1 to 5 substituents each independently selected from the group consisting of hydrogen, halogen, —$OR^{iii}$, —$OC(O)R^{iii}$, —CN, —$C(O)R^{iii}$, —$CO_2R^{iii}$, —$C(O)NR^{iii}R^{iv}$, —$NO_2$, —$NR^{iii}R^{iv}$, —$NR^{iii}C(O)R^{iv}$, —$NR^{iii}CO_2R^{iv}$, —$NR^{iii}S(O)_2R^{iv}$, —$SR^{iii}$, —$S(O)R^{iii}$, —$S(O)_2R^{iii}$, —$S(O)_2NR^{iii}R^{iv}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $R^{iii}$ and $R^{iv}$ may be independently selected from the group consisting of $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the heterocyclic product formed by the enantioselective O-nitroso/aldol reaction between the compound of formula VI and the compound of formula XI is represented by the following structure (XIV):

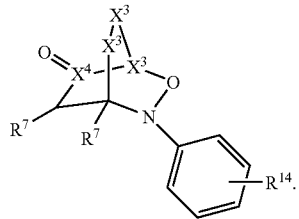

XIV where:

each $R^7$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $X^3$ may independently represent —$CR^{12}R^{13}$—, —$NR^2$—, —O—, or —S—;

$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

each $R^{12}$ and $R^{13}$, together with the atom to which they are attached, may form a 5-, 6- or 7-membered heterocyclic ring; and $X^4$ may represent —C— or —S—;

each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

$R^{14}$ may represent 1 to 5 substituents each independently selected from the group consisting of hydrogen, halogen, —$OR^{iii}$, —$OC(O)R^{iii}$, —CN, —$C(O)R^{iii}$, —$CO_2R^{iii}$, —$C(O)NR^{iii}R^{iv}$, —$NO_2$, —$NR^{iii}R^{iv}$, —$NR^{iii}C(O)R^{iv}$, —$NR^{iii}CO_2R^{iv}$, —$NR^{iii}S(O)_2R^{iv}$, —$SR^{iii}$, —$S(O)R^{iii}$, —$S(O)_2R^{iii}$, —$S(O)_2NR^{iii}R^{iv}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $R^{iii}$ and $R^{iv}$ may be independently selected from the group consisting of $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl In another embodiment, the heterocyclic product formed by the enantioselective O-nitroso/aldol reaction between the compound of formula VII and the compound of formula XI is represented by the following structure (XV):

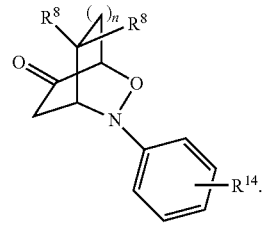

XV where:

each $R^8$ may independently represent a substituent selected from the group consisting of hydrogen, halogen, —$OR^c$, —$OC(O)R^c$, —CN, —$C(O)R^c$, —$CO_2R^c$, —$C(O)NR^cR^d$, —$NO_2$, —$NR^cR^d$, —$NR^cC(O)R^d$, —$NR^cCO_2R^d$, —$NR^cS(O)_2R^d$, —$SR^c$, —$S(O)R^c$, —$S(O)_2R^c$, —$S(O)_2NR^cR^d$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

n may be 0, 1, 2, or 3; and each $R^c$ and $R^d$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

$R^{14}$ may represent 1 to 5 substituents each independently selected from the group consisting of hydrogen, halogen, —$OC(O)R^{iii}$, —$OC(O)R^{iii}$, —CN, —$C(O)R^{iii}$, —$CO_2R^{iii}$, —$C(O)NR^{iii}R^{iv}$, —$NO_2$, —$NR^{iii}R^{iv}$, —$NR^{iii}C(O)R^{iv}$, —$NR^{iii}CO_2R^{iv}$, —$NR^{iii}S(O)_2R^{iv}$, —$SR^{iii}$, —$S(O)R^{iii}$, —$S(O)_2R^{iii}$, —$S(O)_2NR^{iii}R^{iv}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $R^{iii}$ and $R^{iv}$ may be independently selected from the group consisting of $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl In another embodiment, the heterocyclic product formed by the enantioselective O-nitroso/aldol reaction between the compound of formula VIII and the compound of formula XI is represented by the following structure (XVI):

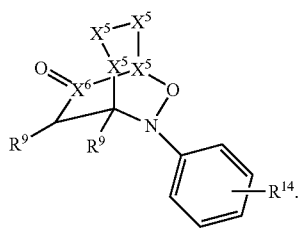

XVI where:
each $R^9$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $X^5$ may independently represent —$CR^{12}R^{13}$—, —$NR^2$—, —O—, or —S—;

$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

each $R^{12}$ and $R^{13}$, together with the atom to which they are attached, may form a 5-, 6- or 7-membered heterocyclic ring; and $X^6$ may represent —C— or —S—;

$R^{14}$ may represent 1 to 5 substituents each independently selected from the group consisting of hydrogen, halogen, —$OR^{iii}$, —$OC(O)R^{iii}$, —CN, —$C(O)R^{iii}$, —$CO_2R^{iii}$, —$C(O)NR^{iii}R^{iv}$, —$NO_2$, —$NR^{iii}R^{iv}$, —$NR^{iii}C(O)R^{iv}$, —$NR^{iii}CO_2R^{iv}$, —$NR^{iii}S(O)_2R^{iv}$, —$SR^{iii}$, —$S(O)R^{iii}$, —$S(O)_2R^{iii}$, —$S(O)_2NR^{iii}R^{iv}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $R^{iii}$ and $R^{iv}$ may be independently selected from the group consisting of $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment, the heterocyclic product formed by the enantioselective O-nitroso/aldol reaction between the compound of formula IX and the compound of formula XI is represented by the following structure (XVII):

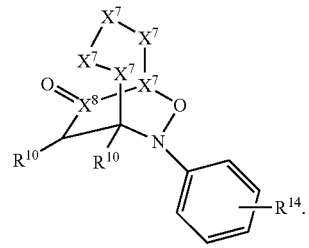

XVII where:
each $R^{10}$ may represent a substituent independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^i$, —$S(O)_2R^i$, —$S(O)_2NR^iR^{ii}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $X^7$ may independently represent —$CR^{12}R^{13}$—, —$NR^2$—, —O—, or —S—;

$R^{12}$ and $R^{13}$ may represent substituents independently selected from the group consisting of hydrogen, halogen, —$OR^i$, —$OC(O)R^i$, —CN, —$C(O)R^i$, —$CO_2R^i$, —$C(O)NR^iR^{ii}$, —$NO_2$, —$NR^iR^{ii}$, —$NR^iC(O)R^{ii}$, —$NR^iCO_2R^{ii}$, —$NR^iS(O)_2R^{ii}$, —$SR^i$, —$S(O)R^{ii}$, —$S(O)_2R^i$, —$S(O)_2NR^iR^{ii}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

each $R^{12}$ and $R^{13}$, together with the atom to which they are attached, may form a 5-, 6- or 7-membered heterocyclic ring; and $X^8$ may represent —C— or —S—;

each $R^i$ and $R^{ii}$ may independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

$R^{14}$ may represent 1 to 5 substituents each independently selected from the group consisting of hydrogen, halogen, —$OR^{iii}$, —$OC(O)R^{iii}$, —CN, —$C(O)R^{iii}$, —$CO_2R^{iii}$, —$C(O)NR^{iii}R^{iv}$, —$NO_2$, —$NR^{iii}R^{iv}$, —$NR^{iii}C(O)R^{iv}$, —$NR^{iii}CO_2R^{iv}$, —$NR^{iii}S(O)_2R^{iv}$, —$SR^{iii}$, —$S(O)R^{iii}$, —$S(O)_2R^{iii}$, —$S(O)_2NR^{iii}R^{iv}$, $C_{1-8}$ alkyl, C2-8 alkenyl, C2-8 alkynyl, $C_{3-8}$ cycloalkyl, $C_{6-10}$ aryl, 5- to 10-membered heteroaryl, and 3- to 10-membered heterocyclyl;

each $R^{iii}$ and $R^{iv}$ may be independently selected from the group consisting of $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl.

In another embodiment of the invention, the enantioselectivity of the α-aminooxyketones and α-aminooxyaldehydes compounds produced by the process of the invention is greater than about 90% ee. Advantageously, enantioselectivity is greater than about 95% ee. More advantageously, the enantioselectivity is greater than 99% ee.

In another embodiment of the invention, the amount of proline-based catalyst used in the process of the invention is less than about 40 mol % but greater than 0 mol %. Advantageously, the amount of proline based catalyst is the range of from about 10 mol % to about 30 mol %. More advantageously, the amount of proline-based catalyst is about 20 mol %.

In another embodiment of the invention, the molar ratio of the amount of nitroso compound to α,β-unsaturated cyclic ketone (enone) is from about 10:1 to about 0.5:1. Advantageously, the molar ratio of the amount of nitroso compound to α,β-unsaturated cyclic ketone (enone) is from about 4:1 to about 1:1. More advantageously, the molar ratio of the amount of nitroso compound to α,β-unsaturated cyclic ketone (enone) is from about 2:1.

The invention also encompasses pharmaceutical compositions that may comprise the α-aminoxyketones, α-hydroxyketones and cyclic α, β unsaturated ketones described herein. In an advantageous embodiment, the invention encompasses anti-cancer or antiviral compositions that may comprise α-aminoxyketones, α-hydroxyketones and cyclic α, β unsaturated ketones, or derivatives thereof, and methods for administering the same.

In one embodiment, the α-aminooxyketones of the present invention may be substituted for its natural equivalent. Such substitutions will be apparent to one of skill in the art. In another embodiment, the α-aminooxyketones of the present invention may be substituted for α-hydroxyketones and their equivalents thereof. Such substitutions will be apparent to one of skill in the art. In another embodiment, the α-hydroxyketones of the present invention may be substituted for its natural aldose equivalent. Such substitutions will be apparent to one of skill in the art.

The compounds of the invention may be useful for treating or preventing a variety of cancers, including, but not limited to, leukemias, including but not limited to acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, Lymphomas including but not limited to Hodgkin's disease, non-Hodgkin's disease, Multiple myeloma, Waldenstrom's macroglobulinemia, Heavy chain disease, Solid tumors including but not limited to sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma.

The compounds of the invention may be useful for treating or preventing a variety of viral infections, including, but not limited to those caused by infection with hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In an advantageous embodiment, the compounds of the present invention, or a derivative thereof, may be useful as an antiviral against against orthopox viruses, such as, but not limited to, smallpox, monkeypox and cowpox (see, e.g., Chu et al., Bioorg Med Chem Lett. 2003 Jan. 6; 13(1):9-12). In another advantageous embodiment, the cyclic α, β unsaturated ketones of the present invention, or a derivative thereof, may be used in the synthesis of nucleosides, nucleotides or derivatives thereof that may be used as antiviral therapeutic agents (see, e.g., Jin & Chu, Nucleosides Nucleotides Nucleic Acids. 2003 May-August; 22 (5-8):771-3).

The compounds of the invention may be useful for treating or preventing several types of inflammation, including, but not limited to, eczema, inflammatory bowel disease, rheumatoid arthritis, asthma, psoriasis, ischemia/reperfusion injury, ulcerative colitis and acute respiratory distress syndrome. In an advantageous embodiment, the compounds of the present invention, or a derivative thereof, may be used as an inhibitor of interleukin-1 biosynthesis (see, e.g., Batt et al., J Med Chem. 1993 May 14; 36(10):1434-42).

In another embodiment, the compounds of the invention are useful for treating or preventing ulcers. For example, urease inhibitors have recently attracted much attention as potential new anti-ulcer drugs (see, e.g., Amtul et al., Curr Med Chem. 2002 July; 9(14):1323-48). Accordingly, the compounds of the invention may be used as an inhibitor of urease activity (see, e.g., Tanaka et al., Bioorg Med Chem. 2004 Jan. 15; 12(2):501-5).

In another embodiment, the compounds of the invention are useful for treating or preventing Alzheimer's disease. Accordingly, the compounds of the invention may be used as an inhibitor of amyloid-beta (Abeta) protein production, and accordingly as a potential treatment for Alzheimer's disease (see, e.g., Wallace et al., Bioorg Med Chem Lett. 2003 Mar. 24; 13(6):1203-6).

In another embodiment, the compounds of the invention may be useful as analgesics. For example, heterocyclic bicyclo[3.3.1]nonan-9-ones were found to have a high affinity to kappa opioid receptors (see, e.g., Brandt et al., Arch Pharm (Weinheim). 1996 June; 329(6):311-23). In another example, 2,4-di-2-pyridyl-substituted 7-methyl-3,7-diazabicyclo [3.3.1]nonan-9-one-1,5-diester was found to have a reasonable kappa-agonistic activity (see, e.g., Holzgrabe & Erciyas, Arch Pharm (Weinheim). 1992 October; 325(10):657-63).

In another embodiment, the compounds of the present invention may be useful in preventing or treating cardiovascular diseases, such as, but not limited to, hypertension, heart failure, pulmonary hypertension and renal diseases. For example, bosentan, an endothelin receptor antagonist, has received approval by the Food and Drug Administration (FDA) for use in pulmonary artery hypertension (see, e.g., Vatter et al., Methods Find Exp Clin Pharmacol. 2004 May; 26(4):277-86). The compounds of the present invention, or a derivative thereof, may be used as an endothelin receptor antagonist (see, e.g., Niiyama et al., Bioorg Med Chem. 2002 November; 10(11):3437-44).

Due to their activity, the compounds of the invention are advantageously useful in veterinary and human medicine.

When administered to a patient, a compound of the invention is preferably administered as component of a composition that optionally comprises a pharmaceutically acceptable vehicle the present compositions, which comprise a compound of the invention, are preferably administered orally. The compositions of the invention may also be administered by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compounds of the invention.

In certain embodiments, the present compositions may comprise one or more compounds of the invention.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin The mode of administration is left to the discretion of the practitioner. In most instances, administration will result in the release of a compound of the invention into the bloodstream.

In specific embodiments, it may be desirable to a compound of the invention locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a compound of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990. Science 249:1527-1533; Treat et al, in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid).

In yet another embodiment, the compounds of the invention can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533) may be used. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target of a compound of the invention, thus requiring only a fraction of the systemic dose.

The present compositions can optionally comprise a suitable amount of a pharmaceutically acceptable vehicle so as to provide the form for proper administration to the patient.

In a specific embodiment, the tern "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening. lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro ed., Mack Publishing Co. Easton, Pa., 19th ed., 1995, pp. 1447 to 1676, incorporated herein by reference.

In a preferred embodiment, the compounds of the invention are formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. Typically, compositions for intravenous administration comprise sterile isotonic aqueous buffer. Where necessary, the compositions may also include a solubilizing agent.

In another embodiment, the compounds of the invention can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compounds of the invention are to be administered by infusion, they can be dispensed, for example, with an infusion bottle containing sterile pharmaceutical grade water or saline. Where the compounds of the invention are administered by injection, an ampoule of sterile water for injection or saline can be provided so that the ingredients may be mixed prior to administration.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed will also depend on the route of administration, and the seriousness of the disease or disorder, and should be decided according to the judgment of the practitioner and each patient's circumstances. However, suitable dosage ranges for oral administration are generally about 0.001 milligram to about 200 milligrams of a compound of the invention or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound of the invention is administered, or if a compound of the invention is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day, Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The invention also provides pharmaceutical packs or kits comprising one or more vessels containing one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a therapeutic agent and a compound of the invention.

The compounds of the invention are preferably assayed in vitro and in vivo, for the desired therapeutic or prophylactic activity, prior to use in humans. For example, in vitro assays can be used to determine whether it is preferable to administer a compound of the invention alone or in combination with another compound of the invention and/or a therapeutic agent. Animal model systems can be used to demonstrate safety and efficacy.

Other methods will be known to the skilled artisan and are within the scope of the invention.

In certain embodiments of the present invention, a compound of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as or in a different composition from that comprising the compound of the invention. In another embodiment, a composition comprising a compound of the invention is administered prior or subsequent to administration of another therapeutic agent. As many of the disorders for which the compounds of the invention are useful in treating are chronic, in one embodiment combination therapy involves alternating between administering a composition comprising a compound of the invention and a composition comprising another therapeutic agent, e.g., to minimize the toxicity associated with a particular drug. The duration of administration of the compound of the invention or therapeutic agent can be, e.g., one month, three months, six months, a year, or for more extended periods. In certain embodiments, when a compound of the invention is administered concurrently with another therapeutic agent that potentially produces adverse side effects including, but not limited to, toxicity, the therapeutic agent can advantageously be administered at a dose that falls below the threshold at which the adverse side is elicited.

The therapeutic agent can be an anti-cancer agent. Useful anti-cancer agents include, but are not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, .gamma.-radiation, alkylating agents including nitrogen mustard such as cyclophosphamide, Ifosfamide, trofosfamide, Chlorambucil, nitrosoureas such as carmustine (BCNU), and Lomustine (CCNU), alkylsulphonates such as busulfan, and Treosulfan, triazenes such as Dacarbazine, platinum containing compounds such as Cisplatin and carboplatin, plant alkaloids including vinca alkaloids, vincristine, Vinblastine, Vindesine, and Vinorelbine, taxoids including paclitaxel, and Docetaxol, DNA topoisomerase inhibitors including Epipodophyllins such as etoposide, Teniposide, Topotecan, 9-aminocamptothecin, campto irinotecan, and crisnatol, mytomycins such as mytomycin C, and Mytomycin C, anti-metabolites, including anti-folates such as DHFR inhibitors, methotrexate and Trimetrexate, IMP dehydrogenase inhibitors including mycophenolic acid, Tiazofurin, Ribavirin, EICAR, Ribonuclotide reductase Inhibitors such as hydroxyurea, deferoxamine, pyrimidine analogs including uracil analogs 5-Fluorouracil, Floxuridine, Doxifluridine, and Ratitrexed, cytosine analogs such as cytarabine (ara C), cytosine arabinoside, and fludarabine, purine analogs such as mercaptopurine, thioguanine, hormonal therapies including receptor antagonists, the anti-estrogens Tamoxifen, Raloxifene and megestrol, LHRH agonists such as goscrclin, and Leuprolide acetate, anti-androgens such as flutamide, and bicalutamide, retinoids/deltoids, Vitamin D3 analogs including EB 1089, CB 1093, and KH 1060, photodyamic therapies including vertoporfin (BPD-MA), Phthalocyanine, photosensitizer Pc4, Demethoxy-hypocrellin A, (2BA-2-DMHA), cytokines including Interferon-.alpha., Interferon-.gamma., tumor necrosis factor, as well as other compounds having anti-tumor activity including Isoprenylation inhibitors such as Lovastatin, Dopaminergic neurotoxins such as 1-methyl-4-phenylpyridinium ion, Cell cycle inhibitors such as staurosporine, Actinomycins such as Actinomycin D and Dactinomycin, Bleomycins such as bleomycin A2, Bleomycin B2, and Peplomycin, anthracyclines such as daunorubicin, Doxorubicin (adriamycin), Idarubicin, Epirubicin, Pirarubicin, Zorubicin, and Mitoxantrone, MDR inhibitors including verapamil, and Ca$^{2+}$ ATPase inhibitors such as thapsigargin.

The therapeutic agent can be an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

The therapeutic agent can be an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, diclofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

The invention will now be further described by way of the following non-limiting examples.

EXAMPLES

The catalyst of formula (IV) can be synthesized using previously known methods in the art. The heterocyclic compound could be synthesized from natural or synthesized proline. The tetrazole derivative shown in formula (IVb) could be synthesized by a reported method (*Tetrahedron Lett.*, vol. 36, 7115-7118, (1995); and *J. Med. Chem.*, vol. 28, 1067-1071, (1985)). Thus, commercially available N-(benzyloxycarbonyl)-L-proline is converted to an amide via a reaction with ammonia and dehydrated with phosphorousoxychloride to give nitrile. The obtained nitrile is treated with sodium azide to give a tetrazole and the Cbz (benzyloxycarbonyl) group is deprotected with HBr/AcOH or Pd/C, H$_2$ to give the tetrazole derivative which is shown in formula (IVa). An example of this preparative scheme is described in detail below:

Preparation of L-Pyrrolidine-2-yl-1H-tetrazole
(Catalyst of Formula (IVa))

Preparation of N-benzyloxycarbonyl-L-prolinamide

Scheme 1

The ammonium hydrogencarbonate (1.26 equiv) was added to the stirred solution of carbobenzyloxy-L-proline (1 equiv), pyridine and Boc$_2$O (1.30 equiv) in acetonitrile and stirred for 20 h. The solvent was removed, and the residue was diluted with ethyl acetate, washed with water, extracted with ethyl acetate, dried over MgSO$_4$ and evaporated in vacuo to afford N-benzyloxycarbonyl-L-prolinamide as colorless crystals. $^1$H NMR (CDCl$_3$, 400 MHz) δ7.36 (m, 5H, Ar—H), 6.71 (s, 1H, NHH), 5.81 (s, 1H, NHH), 5.20 (d, 1H, J=12 Hz, OCHH), 5.15 (d, 1H, J=12 Hz, OCHH), 4.32 (m, 1H, NCH), 3.53 (m, 2H, NCH$_2$), 1.91-2.33 (m, 4H, CH$_2$CH$_2$);

Preparation of N-benzyloxycarbonyl-L-proline nitrile

Scheme 2

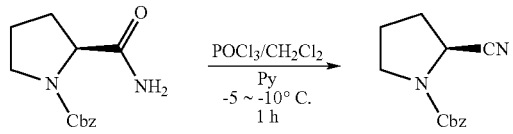

The phosphorus oxychloride in dichloromethane was added over 10 min to the solution of N-benzyloxycarbonyl-L-prolinamide in dry pyridine at −5∼−10° C. under N$_2$. The mixture was stirred at −5∼−10° C. for 1 h and then it was poured on ice and extracted with saturated cupric sulfate solution and saturated sodium chloride solution, dried over MgSO$_4$ and evaporated to in vacuo to afford N-benzyloxycarbonyl-L-proline nitrile as a pale yellow oil. $^1$H NMR (CDCl$_3$, 400 MHz) δ7.96 (d, 2H, J=7.2 Hz, Ar—H), 7.90 (t, 1H, J=7.2 Hz, Ar—H), 7.77 (t, 2H, J=8.0 Hz, Ar—H), 4.80 (t, 1H), 3.28-3.36 (m, 2H), 2.34-2.52 (m, 1H), 2.04-2.20 (m, 3H);

Preparation of N-benzyloxycarbonyl pyrroridine-L-2-yl-1H-tetrazole

Scheme 3

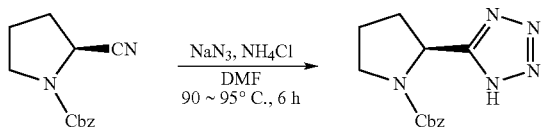

The mixture of N-benzyloxycarbonyl-L-prolinamide (1 equiv), sodium azide (1.04 equiv), ammonium chloride (1.1 equiv), and dry DMF was stirred at 90~95° C. under $N_2$ for 6 h. The mixture was poured onto ice, acidified to pH 2 with diluted HCl, and extracted with $CHCl_3$. The $CHCl_3$ layer was washed with water and saturated sodium chloride, dried over $Na_2SO_4$, and evaporated in vacuo to afford crude material. This crude material was purified with silicagel chromatography to pure N-benzyloxycarbonyl pyrroridine-L-2-yl-1H-tetrazole. $^1$H NMR ($CDCl_3$, 400 MHz) δ7.37 (s, 5H), 5.20 (m, 3H), 3.55 (m, 2H), 2.06-2.34 (m, 4H).

Preparation of L-pyrrolidine-2-yl-1H-tetrazole

Scheme 4

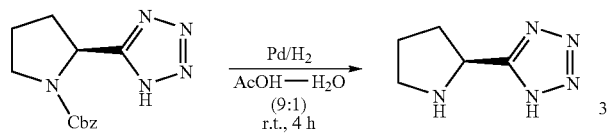

N-benzyloxycarbonyl pyrrolidine-L-2-yl-1H-tetrazole, and 10% palladium on charcoal in acetic acid/water (9:1) was stirred under $H_2$ at room temperature for 4 h. The mixture was filtered through Celite and the filtrate was evaporated in vacuo to afford crude L-pyrrolidine-2-yl-1H-tetrazole, which was recrystallized from acetic acid and diethyl ether. $[\alpha]_D^{25}$+ 14.1° (c=0.12, MeOH); $^1$H NMR ($CD_3OD$, 400 MHz) δ4.82 (m, 2H), 3.33 (m, 2H), 2.39 (m, 1H), 2.02-2.41 (m, 3H); $^{13}$C NMR ($CD_3OD$, 100 MHz) δ159.6, 56.2, 46.6, 31.1, 24.8.

The tetrazole derivative of formula (IVb) could also be prepared by following the reported method from *Organic Letters*, 2001, Vol. 3, No. 25, 4091-4094; *Organic Letters*, 2002, Vol. 4 No. 15, 2525- 2527).

Example 1

General Procedure for the enantioselective O-Nitroso Aldol Reaction Between a ketone and nitrosobenzene in the Presence of (L)-Pyrrolidine-Based tetrazole catalyst of Formula IVb To a room temperature solution of pyrrolidine-based tetrazole catalyst (5 mol %) and ketone (1.5 mmol, 3 eq) in DMSO (1 ml) was added the solution of nitrosobenzene (0.5 mmol, 1 eq) in DMSO (1 mL) dropwise for 1 h. The resulting mixture was stirred at this temperature until the nitrosobenzene was completely consumed (1 h), as determined by TLC (hexane/ ethyl acetate=3/1). The reaction mixture was then poured into an iced saturated $NH_4Cl$ solution. The aqueous layer was extracted with ethyl acetate (20 mL×3). The combined organic extracts were washed with brine, dried over $Na_2SO_4$ with cooling and concentrated under reduced pressure after filtration. The residual crude product was chromatographed on a two-layered column filled with Florisil® (upper layer) and silica gel (lower layer) using a mixture of ethyl acetate and hexane as the eluant to give the product.

Example 2

General Procedure for the Enantioselective O-nitroso aldol Reaction Between an aldehyde and nitrosobenzene in the Presence of (L)-pyrrolidine-Based tetrazole catalyst of Formula IVb To a room temperature solution of pyrrolidine-based tetrazole catalyst (10 mol %) in acetonitrile (1 mL) was added nitrosobenzene (1 equiv, 0.5 mmol) in one portion and stirred at room temperature for 10 min. To this green heterogeneous solution was then added aldehyde (3equiv, 1.5 mmol) in one portion. The resulting mixture was stirred at this temperature until the nitrosobenzene was completely consumed (15~30 min), as determined by TLC (hexane/ethyl acetate=2/1). Then, the reaction was transferred to a methanol suspension of $NaBH_4$ at 0° C. After 20 min, the reaction mixture was then poured into saturated $NH_4Cl$ solution. The aqueous layer was extracted with diethyl ether (20 mL×3). The combined organic extracts were dried over $Na_2SO_4$ with cooling and concentrated under reduced pressure after filtration. The residual crude product was chromatographed on column filled with silica gel using a mixture of ethyl acetate and hexane as the eluant to give the product.

Example 3

Procedure for the synthesis of α-hydroxy cyclohexanone

To a room temperature solution of pyrrolidine-based tetrazole catalyst (5 mol %) and cyclohexanone (3 equiv, 1.5 mmol) in DMSO (1 mL) was added the solution of nitrosobenzene (1 equiv, 0.5 mmol) in DMSO (1 mL) dropwise for 1 h. The resulting mixture was stirred at this temperature until the nitrosobenzene was completely consumed (1 h), as determined by TLC (hexane/ethyl acetate=3/1). After cooling to 0° C., $CuSO_4$ (0.3 eq) and MeOH (3 mL) were added and stirred at 0° C. for 10 h. The reaction mixture was quenched by cooled brine (20 mL) and the aqueous layer was extracted with ethyl acetate (10 mL×3). The combined organic extracts were washed with brine, dried over $Na_2SO_4$ with cooling and concentrated under reduced pressure after filtration. The residual crude product was chromatographed on a silica gel using a mixture of ethyl acetate and hexane as the eluant to give the product.

Example 4

Procedure for the synthesis of 1,2-cyclohexanediol

The solution of α-hydroxy cyclohexanone formed in Example 3 (1 equiv, 0.8 mmol) in MeOH (1 mL) was added to a methanol suspension of $NaBH_4$ at 0° C. and stirred at this temperature for 1 h. Then, the reaction mixture was poured into a saturated $NH_4Cl$ solution. The aqueous layer was extracted with diethyl ether (20 mL×3). The combined organic extracts were dried over $Na_2SO_4$ with cooling and concentrated under reduced pressure after filtration. The residual crude product was chromatographed on a column filled with silica gel using a mixture of ethyl acetate and hexane as the eluant to give the product.

Example 5

Figure 3:
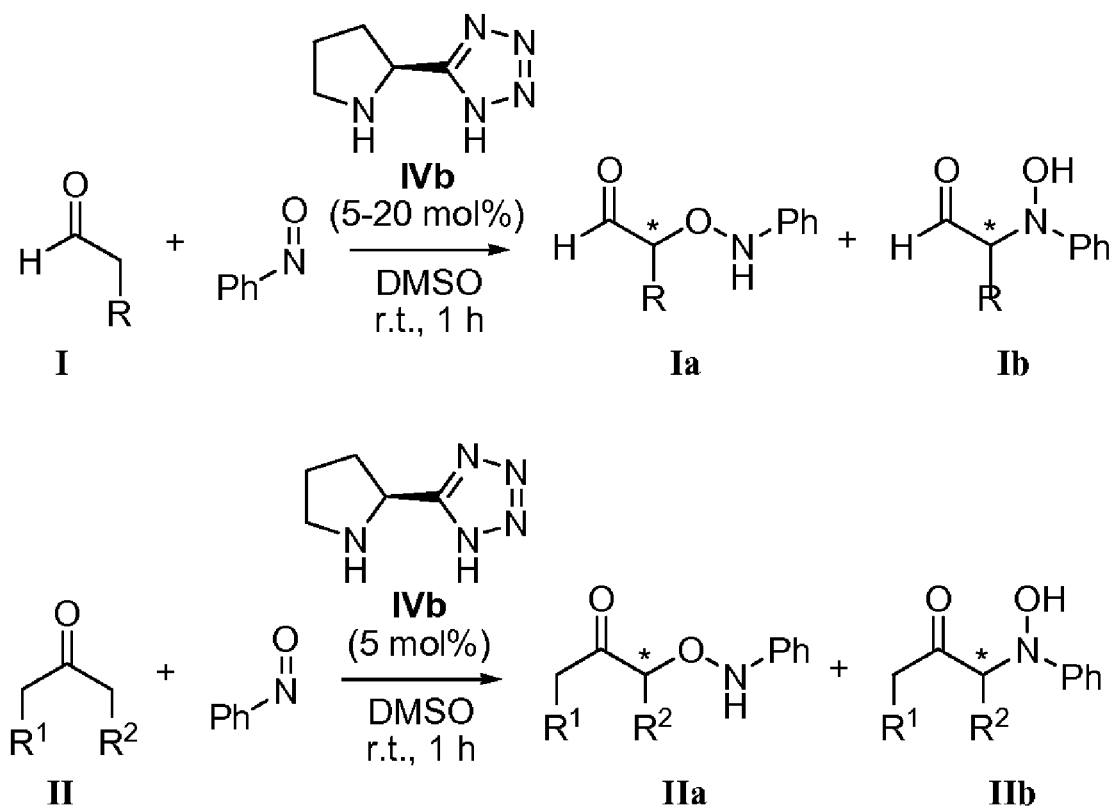

Specific Examples of the Enantioselective O-nitroso aldol Reaction Between ketone or aldehyde and nitrosobenzene in the Presence of (L)-pyrrolidine-Based tetrazole catalyst of Formula IVb The enantioselective O-nitroso aldol between various ketones or aldehydes and nitrosobenzene was investigated (see FIG. 3). The results of these reactions are displayed in Table 1. For reactions with cyclic ketones (examples 5a-5d), optimal results were obtained with 5 mol % of (L)-pyrrolidine-tetrazole catalyst IVb. As shown in Table 1, the reactions between cyclic ketones and nitrosobenzene proceeded cleanly to afford O-adducts IIa in 87-97% yield and with >99% ee. Production of the corresponding N-adducts IIb was negligibe in all cases.

With acyclic ketones (Example 5e) and aldehydes (Examples 5f-5h), the enantioselectivities were still maintained in excellent levels, but yields of O-nitroso aldol products (Ia) were moderate owing in part to the production of the N-adducts. Yields of the desired α-aminooxyketones or α-aminooxyaldehydes could be increased by increasing the amount of catalyst. For example, with 10-20 mol % catalyst, reactions between aldehydes in examples 5f-5h of Table 1 and nitrosobenzene under standard conditions (see footnotes in Table 1) gave 67-75% yield of the desired α-aminooxyaldehydes and a negligible amount of the corresponding N-adduct. Reaction between methyl ethyl ketone (example 5e) and nitrosobenzene in the presence of 20 mol % of the catalyst gave 54% of the desired O-adduct and 21% of the N-adduct.

TABLE 1

Examples of enantioselective O-nitroso aldol reactions between various ketones or aldehydes and nitrosobenzene catalyzed by compound IVb.*

| Entry | Reagent | Example*** | yield, %¶ | ee, % (product)†† | (configuration)§§ |
|---|---|---|---|---|---|
| 1** | cyclohexanone | 5a | 94 | >99 | (S) |
| 2** | tetrahydropyran-4-one | 5b | 87 | >99 | (S) |
| 3** | 1,4-dioxaspiro[4.5]decan-8-one | 5c | 97 | 99 | (S) |
| 4** | N-Cbz-piperidin-4-one (Bn) | 5d | 95 | >99 | (S) |
| 5† | methyl ethyl ketone | 5e | 54 | >99 | (S) |
| 6‡ | 3-phenylpropanal | 5f | 67 | 98 | (R) |
| 7§ | 3-methylbutanal | 5g | 65 | 98 | (R) |
| 8‡ | hexanal | 5h | 69 | 98 | (R) |

*All reactions were conducted with 1.0 equiv of nitrosobenzene, 3 equiv of ketone (or aldehyde), specified mol % of catalyst IVa, and specified solvent at room temperature.
**Performed with 5 mol % of IVb in DMSO.
†Performed with 20 mol % of IVb in DMSO
‡Performed with 10 mol % of IVb in MeCN.
§Performed with 20 mol % of IVb in MeCN,.
***Purifucation procedures, physical data, and spectroscopic data for each individual example are provided below.
¶Isolated yield -Determined by yield of corresponding primary alcohol obtained after reduction of product.
††Determined by chiral HPLC (for separation conditions, refer to examples below).
§Determined after conversion to the corresponding diol (See Example 7 below).

The methods of purifying the products in Table 1 are discussed below. Also provided are the physical and spectroscopic data of the isolated products along with the chiral columns and experimental conditions used to separate the enantiomers of the isolated products. Note that α-aminooxyaldehydes were converted to corresponding primary alcohols to determine yield.

Example 5a

2-(N-Phenyl aminooxy)cyclohexanone

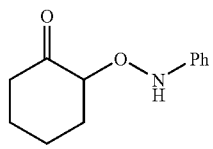

Purification by flash column chromatography with elution by hexane:ethyl acetate (10:1) provided as a yellowish powder. TLC $R_f$=0.30 (3:1 hexane:ethyl acetate); $[\alpha]_D^{27}$+122.0° (c=2.83, CHCl$_3$); IR (CHCl$_3$) 3021, 2951, 2872, 1722, 1603, 1495, 1132, 1100, 1073, 1028, 928 cm$^{-1}$; $^1$H NMR (CDCl$_3$, 300 MHz) δ7.82 (s, 1H, NH), 7.25 (t, 2H, J=8.4 Hz, Ar—H), 6.94 (t, 3H, J=8.1 Hz, Ar—H), 4.35 (q, 1H, J=6.0 Hz, CH), 2.34-2.48 (m, 2H, CH$_2$), 2.00-2.02 (m, 2H, CH$_2$), 1.71-1.79 (m, 4H, CH$_2$); $^{13}$C NMR (CDCl$_3$, 75 MHz) δ209.9, 148.0, 128.8 (2C), 122.0, 114.3 (2C), 86.2, 40.8, 32.5, 27.2, 23.7; Anal. Calcd for C$_{12}$H$_5$NO$_2$: C, 70.22; H, 7.37; N, 6.82. Found: C, 70.22; H, 7.42; N, 6.91. Enantiomeric excess was determined by HPLC with a Chiralcel AD column (40:1 hexane:2-propanol), 1.0 mL/min; major enantiomer t$_r$=34.3 min, minor enantiomer t$_r$=28.1 min.

Example 5b

2-(N-Phenyl aminooxy)tetrahydro-4H-pyran-4-one

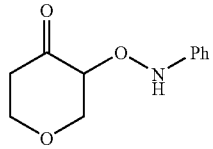

Purification by flash column chromatography with elution by hexane:ethyl acetate (5:1) provided as a yellowish powder. TLC $R_f$=0.079 (5:1 hexane: ethyl acetate); $[\alpha]_D^{27}$+63.0° (c=0.2, CHCl$_3$); IR (CHCl$_3$) 3262, 2990, 2886, 1708, 1659, 1587, 1478, 1273, 1125, 1081, 988, 968, 860 cm$^{-1}$; NMR (CDCl$_3$, 400 MHz) δ7.77 (s, 1H, NH), 7.26 (t, 2H, J=7.8 Hz, Ar—H), 6.97 (t, 1H, J=7.4 Hz, Ar—H), 6.92 (d, 2H, J=7.8 Hz, Ar—H), 4.48-4.52 (m, 1H, CH$_2$), 4.40-4.45 (m, 1H, CH$_2$) 4.16-4.19 (m, 1H, CH), 3.66-3.74 (m, 2H, CH$_2$), 2.66-2.71 (m, 1H, CH$_2$), 2.57 (td, 1H, J=2.9, 14.3 CH$_2$); $^{13}$C NMR (CDCl$_3$, 100 MHz) δ205.4, 147.7, 128.9 (2C), 122.5, 114.7 (2C), 83.5, 70.0, 68.1, 42.3; MS (CI) Exact Mass Calcd for C$_{11}$H$_{13}$NO$_3$ (M+H)$^+$: 208.1. Found: 208.1. Enantiomeric excess was determined by HPLC with a Chiralcel AD-H column (9:1 hexane:2-propanol), 1.0 mL/min; major enantiomer t$_r$=19.8 min, minor enantiomer t$_r$=26.5 min.

Example 5d

1-Phenylacerhyl-3-(N-phenyl aminooxy)piperidin-4-one

Example 5c

7-(N-Phenyl aminooxy)1,4-dioxa-spiro[4.5]decan-8-one

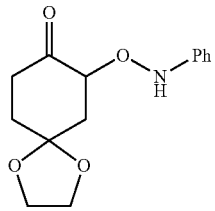

Purification by flash column chromatography with elution by hexane:ethyl acetate (7:1) provided as a yellowish powder. TLC $R_f$=0.18 (3:1 hexane: ethyl acetate); $[\alpha]_D^{27}$+40.6° (c=2.3, CHCl$_3$); IR (CHCl$_3$) 3164, 2989, 1855, 1764, 1580, 1382, 861 cm$^{-1}$; $^1$H NMR (CDCl$_3$, 400 MHz) δ7.84 (s, 1H, NH), 7.24 (t, 2H, J=7.5 Hz, Ar—H), 6.92 (t, 3H, J=8.1 Hz, Ar—H), 4.64 (q, 1H, J =5.7 Hz, CH), 4.05 (s, 4H, CH$_2$), 2.65-2.81 (m, 1H, CH$_2$), 2.42-2.50 (m, 4H, CH$_2$), 1.99-2.05 (m, 1H, CH$_2$); $^{13}$C NMR (CDCl$_3$, 100 MHz) δ210.3, 147.9, 128.8 (2C), 122.0, 114.3 (2C), 107.5, 82.6, 64.6, 64.5, 39.6, 35.9, 34.3; MS (CI) Exact Mass Calcd for C$_{14}$H$_{17}$NO$_4$ (M+H)$^+$: 264.0. Found: 264.10. Enantiomeric excess was determined by HPLC with a Chiralcel OD-H column (9:1 hexane:2-propanol), 0.5 mL/min; major enantiomer t$_r$=20.2 min, minor enantiomer t$_r$=23.2 min.

Example 5d

1-Phenylacethyl-3-(N-phenyl aminooxy)piperidin-4-one

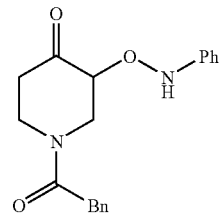

(5d, entry 4, Table 2). Purification by flash column chromatography with elution by hexane:ethyl acetate (3:1) provided as a yellowish oil. TLC $R_f$=0.10 (2:1 hexane:ethyl acetate); $[\alpha]_D^{30}$+25.7° (c=0.7, CHCl$_3$); IR (neat) 3269,3033, 2954, 1710, 1649, 1547, 1480, 1411, 1365, 1277, 1110, 986, 910 cm$^{-1}$; $^1$H NMR (CDCl$_3$, 400 MHz) δ7.75 (bs, 1H, NH), 7.25-7.37 (m, 8H, Ar—H), 7.22 (t, 2H, J=7.5 Hz, Ar—H), 6.94 (t, 2H, J=7.4 Hz, Ar—H), 4.36 (b, 1H, CH), 3.75 (t, 2H, CH$_2$), 3.55 (q, 1H, CH$_2$), 3.37-3.44 (m, 1H, CH$_2$), 2.55 (b, 2H, CH$_2$), 2.41(b, 2H, CH$_2$); $^{13}$C NMR (CDCl$_3$, 100 MHz) δ205.4, 155.1, 136.4, 128.8 (3C), 128.4, 128.2, 127.9 (2C), 122.3, 114.5 (2C), 82.9, 67.9, 64.5, 47.0, 43.7, 42.9, 40.8; MS (CI) Exact Mass Calcd for C$_{19}$H$_{20}$N$_2$O$_3$ (M–H)$^+$: 323.1. Found: 323.1. Enantiomeric excess was determined by HPLC with a Chiralcel AD-H column (9:1 hexane:2-propanol), 1.0 mL/min; major enantiomer $t_r$=36.5 min, minor enantiomer $t_r$=26.0 min.

Example 5e 3-(N-phenyl aminooxy)butan-2-one

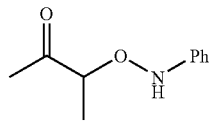

Purification by flash column chromatography with elution by hexane:ethyl acetate (10:1) provided as a yellowish oil. TLC $R_f$=0.20 (5:1 hexane:ethyl acetate); $[\alpha]_D^{25}$+57.4° (c=3.8, CHCl$_3$); IR (neat) 3572, 1815, 1765, 1711, 1582, 1484, 1382, 837, 780 cm$^{-1}$; $^1$H NMR (CDCl$_3$, 400 MHz) δ7.37 (s, 1H, NH), 7.26 (t, 2H, J=7.4 Hz, Ar—H), 6.96 (t, 3H, J=8.5 Hz, Ar—H), 4.43 (q, 1H, CH), 2.20 (s, 3H, CH$_3$), 1.42 (d, 3H, J=7.0 Hz, CH$_3$); $^{13}$C NMR (CDCl$_3$, 100 MHz) δ209.6, 148.2, 129.3 (2C), 122.7, 114.8 (2C), 84.8, 25.9, 15.8; MS (EI) Exact Mass Calcd for C$_{10}$H$_{13}$NO$_2$ (M): 179. Found: 179. Enantiomeric excess was determined by HPLC with a Chiralcel AD-H column (40:1 hexane:2-propanol), 0.5 mL/min; major enantiomer $t_r$=45.2 min, minor enantiomer $t_r$=47.6 min.

3-(N-phenyl hydroxyamino)butan-2-one

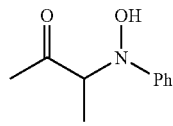

Purification by flash column chromatography with elution by hexane:ethyl acetate (10:1) provided as yellowish oil. TLC $R_f$=0.15 (5:1 hexane:ethyl acetate); $[\alpha]_D^{25}$-6.3° (c=0.12, CHCl$_3$); IR (neat) 3623, 3141, 1855, 1659, 1580, 1468, 1291, 1161, 852 cm$^{-1}$; $^1$H NMR (CDCl$_3$, 400 MHz) δ7.32 (t, 2H, J=7.4 Hz, Ar—H), 7.10 (d, 2H, J=7.7 Hz, Ar—H), 6.97 (t, 1H, J=7.6 Hz, Ar—H), 5.80 (s, 1H, N—OH), 4.24 (q, 1H, J=7.6 Hz, CH), 2.26 (s, 3H, CH$_3$), 1.31 (d, 3H, J=6.7 Hz, CH$_3$); $^{13}$C NMR (CDCl$_3$, 100 MHz) δ209.4, 150.7, 129.3 (2C), 122.3, 116.5 (2C), 69.98, 27.4, 10.8; MS (EI) Exact Mass Calcd for C$_{10}$H$_{13}$NO$_2$ (M): 179. Found: 179. Enantiomeric excess was determined by HPLC with a Chiralcel AD-H column (40:1 hexane:2-propanol), 0.5 mL/min; major enantiomer $t_r$=28.9 min, minor enantiomer $t_r$=25.9 min.

Example 5f

3-Phenyl-2-(N-phenyl aminooxy)-propan-1-ol

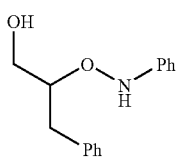

Purification by flash column chromatography with elution by hexane:ethyl acetate (6:1) provided as yellowish oil. TLC $R_f$=0.27 (2:1 hexane:ethyl acetate); $[\alpha]_D^{20}$+26.0 (c=1.07, CHCl$_3$); IR (neat) 3314, 2976, 2862, 1599, 1491, 1452, 1402, 1250, 1105, 1039, 910.5; $^1$H δ7.40-7.12 (m, 8H), 6.94 (t, J= 7.2 Hz, 1H), 6.82 (dd, J=0.9, 8.7 Hz, 1H), 4.13 (dddd, J=2.7, 6.9, 6.3, 6.3 Hz, 1H), 3.85 (dd, J=2.7, 12 Hz, 1H), 3.71 (dd, J=5.7, 12 Hz, 1H), 3.04 (dd, J=6.9, 13.8 Hz, 1H), 2.84 (dd, J=6.9, 13.8 Hz, 1H); $^{13}$C NMR (75 MHz, CDCl$_3$) δ148.2, 137.7, 129.4, 128.9, 128.4, 126.4, 122.3, 114.5, 84.9, 64.1, 36.3; HRMS exact mass calcd for (C$_{12}$H$_{17}$NO$_2$) requires m/z 243.1259, found m/z 243.1251. Enantiomeric excess was determined by HPLC with a Chiralcel AD column (95:5 hexane:ethanol), 1.0 mL/min; major enantiomer $t_r$=42.8 min, minor enantiomer $t_r$=40.1 min.

Example 5g

3-Methyl-2-(N-phenyl aminooxy)-butan-1-ol

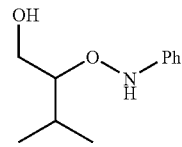

Purification by flash column chromatography with elution by hexane:ethyl acetate (4:1) provided as a yellowish oil. TLC $R_f$=0.22 (2:1 hexane:ethyl acetate); $[\alpha]_D^{20}$+18.3 (c=1.03, CHCl$_3$); IR (neat) 3400, 3269, 3047, 2963, 2878, 1599, 1491, 1468, 1412, 1238, 1051, 1024, 978.0, 908.6, 771.6, 735.0, 694.5 cm$^{-1}$; $^1$H NMR (300 MHz) δ7.38-7.20 (m, 3H), 7.10-6.95 (m, 3H), 3.92-3.85 (m, 2H), 3.80-3.70 (m, 1H), 2.65 (t, J=5.7 Hz, 1H), 2.12-1.95 (m, 1H), 1.05 (d, J=6.9 Hz, 3H), 1.01 (d, J=6.9 Hz, 3H); $^{13}$C NMR (75 MHz, CDCl$_3$) δ148.2, 128.9, 122.3, 114.8, 88.5, 63.4, 28.6, 18.7, 18.5; HRMS exact mass calcd for (C$_{11}$H$_{17}$NO$_2$) requires m/z 195.1259, found m/z 195.1239. Enantiomeric excess was determined by HPLC with a Chiralcel AD column (95:5 hexane:ethanol), 1.0 mL/min; major enantiomer $t_r$=16.2 min, minor enantiomer $t_r$=14.8 min.

Example 5h 2-(N-Phenyl aminooxy)-hexan-1-ol

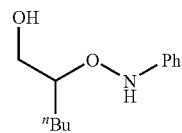

Purification by flash column chromatography with elution by hexane:ethyl acetate (6:1) provided as a yellowish oil. TLC $R_f$=0.36 (2:1 hexane:ethyl acetate); $[\alpha]_D^{20}$+14.1 (c=1.08, CHCl$_3$); IR (neat) 3377, 3144, 2955, 1601, 1493, 1464, 1377, 1240, 1030, 902.8, 769.7; $^1$H NMR (300 MHz, CDCl$_3$) δ7.34-7.20 (m, 2H), 7.04-6.94 (m, 3H), 3.96 (dddd, J=2.4, 6.6, 6.6, 6.6 Hz, 1H), 3.91-3.72 (m, 2H), 2.48 (m, 1H), 1.80-1.20 (m, 7H), 0.92 (t, J=6.6 Hz, 3H); $^{13}$C NMR (75 MHz, CDCl$_3$) δ148.3, 128.8, 122.1, 114.5, 83.8, 64.9, 29.5, 27.8, 22.7, 13.8; HRMS exact mass calcd for (C$_{12}$H$_{19}$NO$_2$) requires m/z 209.1416, found m/z 209.1401. Enantiomeric excess was determined by HPLC with a Chiralcel AD column (95:5 hexane:ethanol), 1.0 mL/min; major enantiomer $t_r$=19.5 min, minor enantiomer $t_r$=17.9 min.

Example 6

Figure 4:
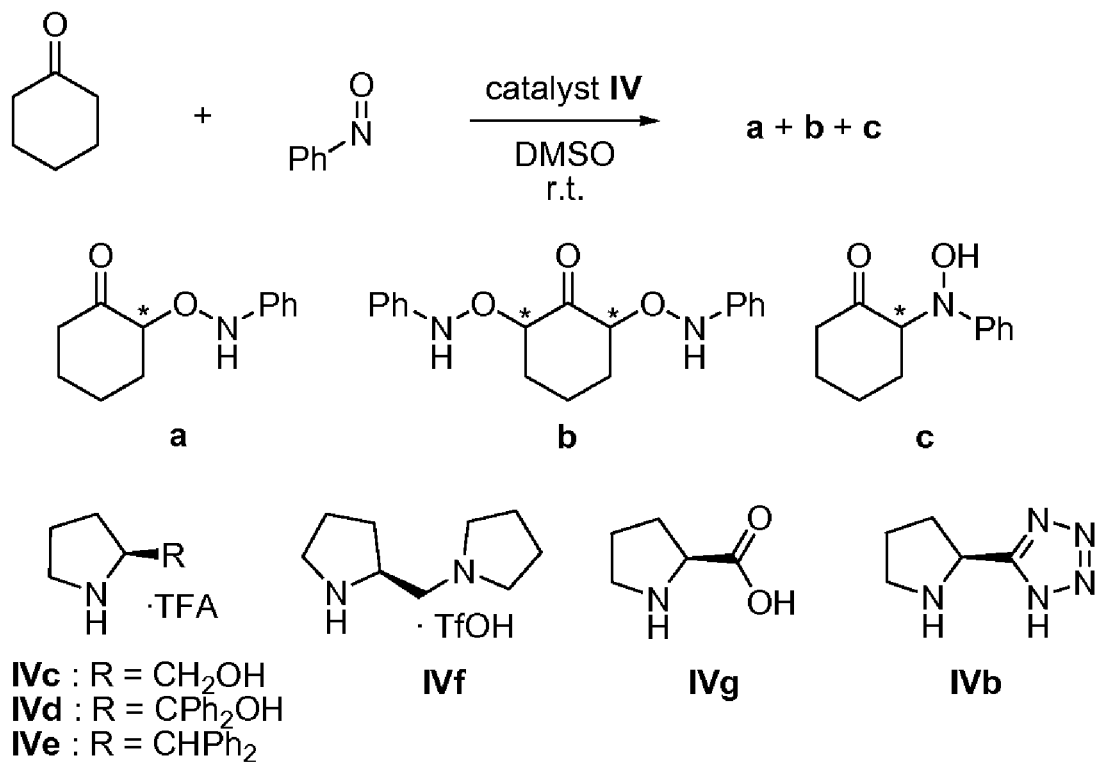
FIG. 4. Comparison of effects of different catalysts of formula (IV).

Comparison of Different (L)-Pyrrolidine Catalysts in the enantioselective O-nitroso aldol Reaction Between cyclohexanone and nitrosobenzene With the O-nitroso aldol reaction between cyclohexanone and nitrosobenzene as a model reaction, several different (L)-pyrrolidone catalysts were assessed. The general reaction scheme and the different catalysts employed are displayed in FIG. 4. The results with various catalysts are summarized in Table 2. Notably, several kinds of substituted pyrrolidine catalysts (IVc-IVe) were unable to catalyze the nitroso aldol process after 1 day at room temperature. The diamine-protonic acid catalyst (IVf) afforded O-adduct with R configuration, but did not provide catalyst turnover. (L)-proline (IVg) and pyrrolidine-based tetrazole (IVb) afforded promising level of regioselection and enantioselection with S configuration for the O-nitroso aldol adduct. Catalyst IVb was particularly attractive in terms of higher reactivity.

Figure 5:
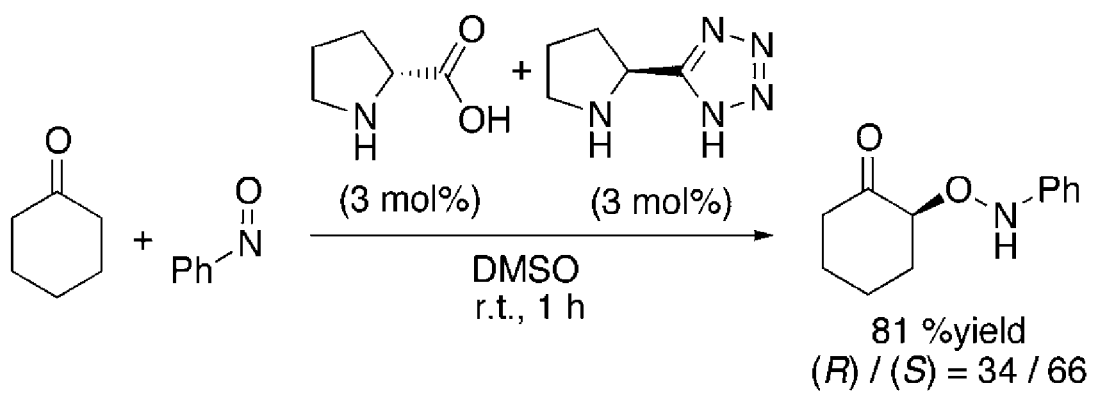
FIG. 5. Effect of mixed catalysts on product formation.

The difference of reactivity in O-nitroso Aldol reactions catalyzed by equal amounts different proline compounds was demonstrated by adding both (D)-proline and catalyst IVb (L-configuration) to the reaction between cyclohexanone and nitrosobenzene. The two catalysts would generate the same product, albeit with different handedness. The reaction scheme is shown in FIG. 5. Clearly, the (S)-enantiomer is the dominant product. Hence, compound IVb catalyzes the O-nitroso Aldol reaction at a rate faster than the same reaction catalyzed by proline itself.

TABLE 2

Catalyst survey of O-nitroso aldol reaction.*

| entry | catalyst (mol %) | time | yield, %† | a/b/c | ee of a, %§ | (conf.)¶ |
|---|---|---|---|---|---|---|
| 1 | IVc (5) | 1 day | <1 | | | |
| 2 | IVd (5) | 1 day | <1 | | | |
| 3 | IVe (5) | 1 day | <1 | | | |
| 4 | IVf (5) | 1 h | 4 | >99/—/— | 37 | (R) |
| 5 | IVg (5) | 1 h | 35 | 98/—/2- | >99 | (S) |
| 6 | IVb (5) | 1 h | 94 | >99/—/— | >99 | (S) |
| 7 | IVb (3) | 1 h | 72 | >99/—/— | >99 | (S) |
| 8 | IVb (2) | 1 h | 50 | >99/—/— | >99 | (S) |

*Reactions were conducted with catalytic amount of IV, 1.0 equiv of nitrosobenzene, and 3 equiv of cyclohexanone in DMSO at room temperature.
†Isolated yield.
§Determined by HPLC, CHIRALPAK AD.
¶Determined after conversion to the corresponding diol (see Example 7 below).

Example 7

Determination of the Absolute Configuration of α-hydroxyketones

The absolute configuration of α-aminooxy compounds were determined by reduction to the corresponding diols. FIG. 6A shows an example of conversion of a ketone into a 1,2-diol. First, the ketone is converted into an enantioenriched α-aminooxyketone through an enantioselective O-nitroso aldol reaction. Reactions with $CuSO_4$ afford the corresponding α-hydroxyketone product. Reduction of the α-hydroxyketone with $NaBH_4$ gives the diol product. FIG. 6B shows an example of conversion of aldehyde into a 1,2-diol. Here, the sequence of reduction with $CuSO_4$ and $NaBH_4$ is reversed relative to the reaction with ketone.

Examples of the α-aminooxyaldehydes which can be obtained by this invention include but are not limited to:
(N-isobutylaminooxy)acetaldehyde,
[N-(1,1-dimethylbutyl)]aminooxyacetaldehyde,
(N-phenylaminooxy)acetaldehyde,
2-(N-isobutylaminooxy)propanal,
2-[N-(1,1-dimethylbutyl)aminooxy]propanal,
2-N-phenylaminooxypropanal,
2-(N-isobutylaminooxy)butanal,
2-[N-(1,1-dimethylbuthyl)aminooxy]-2-methylpropanal,
2-(N-phenylaminooxy)2-methylpropanal,
2-(N-isobutylaminooxy)-4-methylbutanal,
2-[N-(1,1-dimethylbutyl)aminooxy-4-methylbutanal,
2-(N-phenylaminooxy)-4-methylbutanal 2-(N-isobutylaminooxy)hexanal,
2-[N-(1,1-dimethylbutyl)aminooxyhexanal,
2-(N-phenylaminooxy)hexanal, 2-(N-isobutylaminooxy)heptanal,
2-[N-(1,1-dimethylbutyl)aminooxyheptanal,
2-(N-phenylaminooxy)heptanal,
2-(N-isobutylaminooxy)octanal,
2-[N-(1,1-dimethylbutyl)aminooxyoctanal,
2-(N-phenylaminooxy)octanal,
2-(N-isobutylaminooxy)nonanal,
2-[N-(1,1-dimethylbutyl)aminooxynonanal,
2-(N-phenylaminooxy)nonanal,
2-(N-isobutylaminooxy)decanal,
2-[N-(1,1-dimethylbutyl)aminooxydecanal,
2-(N-phenylaminooxy)decanal,
2-(N-isobutylaminooxy)undecanal,
2-[N-(1,1-dimethylbutyl)aminooxyundecanal,
2-(N-phenylaminooxy)undecanal,
2-(N-isobutylaminooxy)dodecanal,
2-[N-(1,1-dimethylbutyl)aminooxydodecanal,
2-(N-phenylaminooxy)dodecanal,
2-(N-isobutylaminooxy)tridecanal,
2-[N-(1,1-dimethylbutyl)aminooxytridecanal; and
2-(N-phenylaminooxy)tridecanal.

Examples of compounds which can be obtained as α-aminooxyaldehydes include but are not limited to:
2,3-bis (N-isobutylaminooxy)butanedial,
2,3-bis[N-1,1-dimethylbutyl]aminooxy]butanedial,
2,3-bis[N-phenylaminooxy]butanedial,
2-N-isobutylaminooxy-2-propenal,
2-N-(1,1-dimethylbutyl)aminooxy-2-propenal,
2-N-phenylaminooxy-2-propenal,
2-N-isobutylaminooxy-2-butenal,
2-N-(1,1-dimethylbutyl)aminooxy-2-butenal,
2-N-phenylaminooxy-2-butenal,
3-phenyl-2-N-isobutylaminooxy-2-propenal,
3-phenyl-2-N-(1,1-dimethylbutyl)aminooxy-2-propenal; and
3-phenyl-2-N-phenylaminooxy-2-propenal.

Examples of the α-aminooxyketones which can be obtained by this invention include but are not limited to:
(N-isobutylaminooxy)acetone,
[N-(1,1-dimethylbutyl)aminooxy]acetone,
(N-phenylaminooxy)acetone,
3-(N-isobutylaminooxy)butane-2-one,
3-[N-(1,1dimethylbutyl)aminooxy]butane-2-one,
(N-phenylaminooxy)butane-2-one,
3-(N-isobutylaminooxy)pentane-2-one,
3-[N-(1,1dimethylbutyl)aminooxy]pentane-2-one,
(N-phenylaminooxy)pentane-2-one,
3-(N-isobutylaminooxy)-4-methylbutane-2-one,
3-[N-(1,1dimethylbutyl)aminooxy]-4-methylbutane-2-one,
(N-phenylaminooxy)-4-methylbutane-2-one,
3-(N-isobutylaminooxy)hexane-2-one,
3-[N-(1,1dimethylbutyl)aminooxy]hexane-2-one,
(N-phenylaminooxy)hexane-2-one,
3-(N-isobutylaminooxy)-4-methylpentane-2-one,
3-[N-(1,1dimethylbutyl)aminooxy]-4-methylpentane-2-one,
(N-phenylaminooxy)-4-methylpentane-2-one,
3-(N-isobutylaminooxy)-pentane-3-one,
3-[N-(1,1dimethylbutyl)aminooxy]-pentane-3-one,
(N-phenylaminooxy)-pentane-3-one,
3-(N-isobutylaminooxy)-2,4-dimethylpentane-3-one,
3-[N-(1,1dimethylbutyl)aminooxy]-2,4-dimethylpentane-3-one,
(N-phenylaminooxy)-2,4-dimethylbutane-3-one,
3-(N-isobutylaminooxy)undecane-2-one,
3-[N-(1,1dimethylbutyl)aminooxy]undecane-2-one; and (N-phenylaminooxy)undecane-2-one.

Examples of the α-aminooxyketones which can be obtained in this invention include but are not limited to:
3-N-isobutylaminooxy-2-butene-2-one,
3-N-(1,1-dimethylbutyl)aminooxy-3-butene-2-one,
3-N-phenylaminooxy-3-butene-2-one,
3-N-isobutylaminooxy-4-methyl-3-pentene-2-one,
3-N-(1,1-dimethylbutyl)aminooxy-4-methyl-3-pentene-2-one,
3-N-phenylaminooxy-4-methyl-3-pentene-2-one,
1-fluoro-1-(N-isobutylaminooxy)acetone,
1-fluoro-1-[N-(1,1dimethylbutyl)aminooxy]acetone,
1-fluoro-1-(N-phenylaminooxy)acetone,
1-chloro-1-(N-isobutylaminooxy)acetone,
1-chloro-1-{N-(1,1dimethylbutyl)aminooxy}acetone,
1-chloro-1-(N-phenylaminooxy)acetone,
3-(N-isobutylaminooxy)-2,4-pentanedione,
3-[N-(1,1-dimethylbutyl)aminooxy]-2,4-pentanedione,
3-(N-phenylaminooxy)-2,4pentanedione,
3-(N-isobutylaminooxy)cyclobutanone,
3-[N-(1,1-dimethylbutyl)aminooxy]cyclobutanone,
3-(N-phenylaminooxy)cyclobutanone,
3-(N-isobutylaminooxy)cyclopentanone,
3-[N-(1,1-dimethylbutyl)aminooxy]cyclopentanone,
3-(N-phenylaminooxy)cyclopentanone,
3-(N-isobutylaminooxy)cyclohexanone,
3-[N-(1,1-dimethylbutyl)aminooxy]cyclohexanone,
3-(N-phenylaminooxy)cyclohexanone,
3-(N-isobutylaminooxy)-2-methylcyclohexanone,
3-[N-(1,1-dimethylbutyl)aminooxy]-2-methylcyclohexanone,
3-(N-phenylaminooxy)-2-methylcyclohexanone,
3-(N-isobutylaminooxy)cyclodecanone,
3-[N-(1,1-dimethylbutyl)aminooxy]cyclodecanone,
3-(N-phenylaminooxy)cyclodecanone,
3-(N-isobutylaminooxy)-2-norbornanone,
3-[N-(1,1-dimethylbutyl)aminooxy]-2-norbornanone,
3-(N-phenylaminooxy)-2-norbornanone,
3-(N-isobutylaminooxy)-2-adamantanone,
3-[N-(1,1-dimethylbutyl)aminooxy]-2-adamantanone,
3-(N-phenylaminooxy)-2-adamantanone.
2-(N-isobutylaminooxy)-4-tetrahydropyranone,
2-[N-(1,1-dimethylbutyl)aminooxy]-4-tetrahydropyranone,
2-(N-phenylaminooxy)-4-tetrahydropyranone,
7-(N-isobutylaminooxy)-spiro[4.5]-1,4-dioxy-decane-8-one,
7-[N-(1,1-dimethylbutyl)aminooxy]spiro[4.5]-1,4-dioxydecane-8-one,
3-(N-isobutylaminooxy)-1-benzylcarbonylpiperidine-4-one,
3-[N-(1,1-dimethylbutyl)aminooxy]-1-benzylcarbonylpiperidine-4-one,
3-(N-phenylaminooxy)-1-benzylcarbonylpiperidine-4-one,
3-(N-isobutylaminooxy)-4-phenylbutane-2-one,
3-[N-(1,1-dimethylbutyl)aminooxy-4-phenylbutane-2-one,
3-(N-phenylaminooxy)-4-phenylbutane-2-one,
2-(N-isobutylaminooxy)-1-indanone,
2-[N-(1,1-dimethylbutyl)aminooxy-1-indanone,
2-(N-phenylaminooxy)-1-indanone,
1-(N-isobutylaminooxy)-2-indanone,
1-[N-(1,1-dimethylbutyl)aminooxy-2-indanone,
1-(N-phenylaminooxy)-2-indanone,
2-(N-isobutylaminooxy)-1-ketotetrahydronaphthalene,
2-[N-(1,1-dimethylbutyl)aminooxy-1-ketotetrahydronaphthalene,
1-(N-phenylaminooxy)-1-ketotetrahydronaphthalene,
1-(N-isobutylaminooxy)-2-ketotetrahydronaphthalene,
1-[N-(1,1-dimethylbutyl)aminooxy-2-ketotetrahydronaphthalene,
1-(N-phenylaminooxy)-2-ketotetrahydronaphthalene,
1-(N-isobutylaminooxy)-7-methoxy-2-ketotetrahydronaphthalene,
1-[N-(1,1-dimethylbutyl)aminooxy-7-methoxy-2-ketotetrahydronaphthalene,
1-(N-phenylaminooxy)-7-methoxy-2-ketotetrahydronaphthalene,
2'-(N-isobutylaminooxy)-1'-acetophenone,
2'-[N-(1,1-dimethylbutyl)aminooxy]-1'-acetophenone,
2'-(N-phenylaminooxy)-1'-acetophenone,
2'-(N-isobutylaminooxy)-1'-propiophenone,
2'-[N-(1,1-dimethylbutyl)aminooxy]-1'-propiophenone,
2'-(N-phenylaminooxy)-1'-propiophenone,
2-(N-isobutylaminooxy)-1,2-bisphenylethane-1-one,
2-[N-(1,1-dimethylbutyl)aminooxy]-1,2-bisphenylethane-1-one,
2-(N-phenylaminooxy)-1,2-bisphenylethane-1-one,
1-(N-isobutylaminooxy)-1,2-bisphenylbutane-1-one,
1-[N -(1,1-dimethylbutyl)aminooxy]-1,2-bisphenylbutane-1-one,
1-(N-phenylaminooxy)-1,2-bisphenylbutane-1-one,
6-(N-isobutylaminooxy)-3,4-dimethylacetophenone,
6-[N-(1,1-dimethylbutyl)aminooxy]-3,4-dimethylacetophenone,
6-(N-phenylaminooxy)-3,4-dimethylacetophenone,
3'-(N-isobutylaminooxy)-2'-acetonaphthone,
3'-[N-(1,1-dimethylbutyl)aminooxy]-2'-acetonaphthone,
3'-(N-phenylaminooxy)-2'-acetonaphthone,
3'-(N-isobutylaminooxy)-2'-chloroacetonaphthone,
3'-[N-(1,1-dimethylbutyl)aminooxy]-2'-chloroacetonaphtone; and
3'-(N-phenylaminooxy)-2'-chloroacetonaphtone.

Example 8

Enantioselective O-Nitroso Aldol/Michael Reactions

General Procedures

All non-aqueous reactions were carried out in oven- or flame-dried glassware under an atmosphere of dry nitrogen unless otherwise noted. Except as otherwise indicated, all reactions were magnetically stirred and monitored by analytical thin-layer chromatography using Whatman pre-coated silica gel flexible plates (0.25 mm) with $F_{254}$ indicator or Merck pre-coated silica gel plates with $F_{254}$ indicator. Visualization was accomplished by UV light (256 nm), with combination of potassium permanganate and/or Ninhydrin and/or phosphomolybdic acid, and/or ferric chloride solution as a indicator. Flash column chromatography was performed according to the method of Still using silica gel 60 (mesh 230-400) supplied by E. Merck. Yields refer to chromatographically and spectrographically pure compounds, unless otherwise noted.

Commercial grade reagents and solvents were used without further purification except as indicated below. Tetrahydrofuran (THF), and Ethylene glycol diethyl ether were distilled from sodium-benzophenone ketyl under an atmosphere of dry argon. 2-Cyclohepetene-1-one was distilled under $P_2O_5$. 1,4-Dioxaspiro[4,5]dec-6-en-8-one was prepared according to reported method (Kerr, W. J.; McLaughlin, M.; Morrison, A. J.; Pauson, P. L. *Org. Lett*, 2001, 3, 2945-2948).

Infrared spectra were recorded as thin films on sodium chloride plates using a Nicolet 20 SXB FTIR. $^1$H NMR and $^{13}$C NMR spectra were recorded on a Bruker Avance 400 (400 MHz $^1$H, 100 MHz $^{13}$C), a Bruker Avance 500 (500 MHz $^1$H, 125 MHz $^{13}$C). Chemical shift values (δ) are reported in ppm relative to Me$_4$Si (δ0.0 ppm). The proton spectra are reported as follows δ (multiplicity, number of protons, coupling constant J). Multiplicities are indicated by s (singlet), d (doublet), t (triplet), q (quartet), p (pentet), h (heptet), m (multiplet) and br (broad).

To the catalyst (0.40 mol) was added enone (2.0 mmol), nitrosobenzene (4.0 mmol) and acetonitrile (4.0 mL). The mixture was allowed to warm to 40° C. and was stirred at the same temperature for 15 hours. The reaction mixture was concentrated under reduced pressure and the residue was purified by silica gel chromatography to afford the Diels Alder adduct.

EXAMPLES

The following Table and examples further demonstrate the scope of the present invention. Table 3 demonstrates that the present invention can be performed with a variety of cyclic α,β-unsaturated ketones and nitroso substrates. Furthermore, the results provided in Table 3 reveal that the heterocyclic product can be obtained in good yields with very high enantioselectivities.

TABLE 3

Reaction Scope[a]

| entry | Example | enone | R, R | ArN=O | yield, %[b] | ee, %[c] |
|---|---|---|---|---|---|---|
| 1 | 8a | | 1a: Me, Me | 2a | 64 | 99 |
| 2 | 8b | | 1b: H, H | 2a | 34 | 99 |
| 3 | 8c | | 1c: Ph, Ph | 2a | 56 | 99 |
| 4 | 8d | | 1d: -(OCH$_2$CH$_2$O)— | 2a | 61 | 98 |
| 5 | 8e | | 1a | 2b | 47 | 98 |
| 6 | 8f | | 1a | 2c | 52 | 98 |
| 7 | 8g | | 1a | 2d | 50 | 99 |
| 8 | 8h | 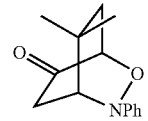 | 1e: H, H | 2a | 14 | 99 |
| 9 | 8i | | 1e: H, H | 2a | 51 | 99 |

[a]Reaction was conducted with 20 mol % of catalysit, 1 equiv of enone and 2 equiv of nitrosobenzene under N$_2$ atomsphere at 40° C. for 15 h.
[b]Isolated yield.
[c]ee value was determined by chiral HPLC.
[d](L)-Proline was used as catalyst.

The methods of purifying the products in Table 3 are discussed below. Also provided are the physical and spectroscopic data of the isolated products along with the chiral columns and experimental conditions used to separate the enantiomers of the isolated products.

Example 8a 8,8-Dimethyl-3-phenyl-2-oxa-3-aza-bicyclo[2.2.2]octan-6-one

Purification by flash column chromatography with elution by (1:9 EtOAc:Hexane) provided as a yellowish oil (64% yield, 99% ee). TLC R$_f$ 0.7 (EtOAc/Hexane, 1:5); [α]$_D^{29}$+82.3° (c=1.10, CHCl$_3$); FTIR (CD$_3$Cl) υ$_{max}$ 2962, 1743, 1595, 1489, 1028, 992 cm$^{-1}$; $^1$H NMR (400 MHz, CDCl$_3$) δ 7.31 (t, J=7.4 Hz, 2H), 7.09 (d, J=8.7 Hz, 2H), 7.00 (t, J=7.3 Hz, 2H), 4.18-4.19 (m, 1H), 3.51-3.53 (m, 1H), 2.71 (dd, J=18.7 Hz, J=2.7 Hz, 1H), 2.48 (dd, J=18.7 Hz, J=3.0 Hz, 1H), 2.31 (dd, J=14.5 Hz, J=3.9 Hz, 1H), 1.81 (dd, J=14.5 Hz, J=1.8 Hz, 1H), 1.57 (s, 3H), 1.47 (s, 3H); $^{13}$C NMR (100 MHz, CD$_3$Cl) δ 208.1, 149.9, 128.9, 122.4, 116.6, 78.2, 68.4, 39.8, 34.9, 33.1, 28.6, 27.2; MS (CI) Exact Mass Calcd for C$_{14}$H$_{15}$N$_2$O$_4$ (M+H)$^+$: 232.1. Found: 232.1. Enantiometric excess was determined by HPLC with Chiralcel AD-H column (97:3 hexane:2-propanol), 0.8 mL/min; major enantiomer t$_r$=11.1 min, minor enantiomer t$_r$=10.6 min. Enantiomer was obtained as a yellowish oil using D-tetrazole catalysis using the same method. (61% yield, 99% ee). [α]$_D^{29}$−79.7° (c=0.56, CHCl$_3$).

Example 8b

3-Phenyl-2-oxa-3-aza-bicyclo[2.2.2]octan-6-one

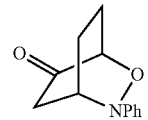

Purification by flash column chromatography with elution by (1:4 EtOAc:Hexane) provided as a yellowish oil (34% yield, 99% ee); TLC $R_f$ 0.5 (EtOAc/Hexane 1:3); $[\alpha]_D^{27}$ −216.9° (c=0.6, CHCl$_3$); FTIR (CD$_3$Cl) $\upsilon_{max}$ 2965, 1745, 1596, 1488, 1306, 1220, 1174, 986 cm$^{-1}$; $^1$H NMR (500 MHz, CD$_3$Cl) δ 7.31 (t, J=7.4 Hz, 2H), 7.12 (d, J=8.7 Hz, 2H), 7.00 (t, J=7.3 Hz, 1H) 4.19-4.22 (m, 2H), 3.02 (br d, J=18.2 Hz, 1H), 2.47 (dd, J=18.1 Hz, J=3.1 Hz, 1H) 2.26-2.40 (m, 2H), 1.91-1.99 (m, 1H), 1.61-1.68 (m, 1H); $^{13}$C NMR (100 MHz, CD$_3$Cl) δ 207.1, 150.3, 129.0, 122.2, 116.2, 76.9, 56.1, 41.8, 22.4, 21.5; MS (CI) Exact Mass Calcd for C$_{13}$H$_{15}$NO$_2$ (M+H)$^+$: 204.1. Found: 204.1. Enantiometric excess was determined by HPLC with Chiralcel AD-H column (90:10 hexane:2-propanol), 1.0 mL/min; major enantiomer t$_r$=23.4 min, minor enantiomer t$_r$=10.0 min.

Example 8c 3,8,8-Triphenyl-2-oxa-3-aza-bicyclo[2.2.2]octan-6-one

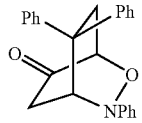

Purification by flash column chromatography with elution by (1:1 Hexane:CH$_2$Cl$_2$) provided as a yellowish crystal (56% yield, 99% ee); TLC $R_f$ 0.7 (CH$_2$Cl$_2$); $[\alpha]_D^{30}$ +288.4° (c=0.97, CHCl$_3$); FTIR (CD$_3$Cl) $\upsilon_{max}$ 3058, 2361, 2337, 1743, 1596, 1449, 1394, 1032, 998, 909 cm$^{-1}$; $^1$H NMR (500 MHz, CD$_3$Cl) δ 7.31 (t, J=7.4 Hz, 2H), 7.04 (d, J=8.8 Hz, 2H), 6.92 (t, J=7.4 Hz, 1H) 4.60 (br d, J=5.8 Hz, 1H), 4.36-4.39 (m, 1H), 2.98 (dd, J=18.1 Hz, J=5.5 Hz, 1H), 2.43 (dd, J=18.1 Hz, J=2.1 Hz, 1H) 2.07-2.16 (m, 3H), 1.86-1.96 (m, 1H), 1.42-1.56 (m, 1H); $^{13}$C NMR (100 MHz, CD$_3$Cl) δ 207.5, 150.0, 129.0, 121.0, 114.7, 83.6, 56.9, 38.8, 30.9, 29.7, 18.9; MS (CI) Exact Mass Calcd for C$_{13}$H$_{15}$NO$_2$ (M+H)$^+$: 355.2. Found: 355.1. Enantiometric excess was determined by HPLC with Chiralcel AD-H column (95:5 hexane:2-propanol), 1.0 mL/min; major enantiomer t$_r$=10.1 min, minor enantiomer t$_r$=8.8 min.

Example 8d 8,12-Dioxaspiro-3-phenyl-2-oxa-3-aza-bicyclo[2,2,2]octan-6-one

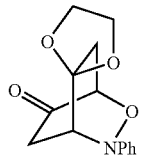

Purification by flash column chromatography with elution by (1:19 EtOAc: CH$_2$Cl$_2$) provided as a yellowish oil (61% yield, 98% ee); TLC $R_f$ 0.6 (EtOAc/CH$_2$Cl$_2$, 1:19); $[\alpha]_D^{28}$ −5.4° (c=1.03, CHCl$_3$); FTIR (CD$_3$Cl) $\upsilon_{max}$ 2979, 2892, 1747, 1597, 1489, 1227, 1064 cm$^{-1}$; $^1$H NMR (500 MHz, CD$_3$Cl) δ 7.31 (t, J=7.4 Hz, 2H), 7.13 (d, J=8.8 Hz, 2H), 7.02 (t, J=7.3 Hz, 1H) 4.32 (dd, J=3.6 Hz, J=2.6 Hz, 1H), 4.10-4.15 (m, 1H), 3.97-4.04 (m, 3H), 3.92 (t, J=2.9 Hz, 1H), 2.91 (dd, J=15.2 Hz, J=3.9 Hz, 1H), 2.88 (dd, J=18.5 Hz, J=2.9 Hz, 1H) 2.66 (dd, J=18.5 Hz, J=2.9 Hz, 1H), 2.28 (dd, J=15.2 Hz, J=2.4 Hz, 1H); $^{13}$C NMR (100 MHz, CD$_3$Cl) δ 204.9, 148.9, 128.8, 122.9, 116.8, 105.5, 77.9, 64.9, 64.8, 64.4, 38.7, 64.5; MS (CI) Exact Mass Calcd for C$_{14}$H$_{15}$N$_2$O$_4$ (M+H)$^+$: 262.1. Found: 262.1. Enantiometric excess was determined by HPLC with Chiralcel AD-H column (90:10 hexane:2-propanol), 1.0 mL/min; major enantiomer t$_r$=20.5 min, minor enantiomer t$_r$=17.3 min.

Example 8e 8,8-Dimethyl-3-p-tolyl-2-oxa-3-aza-bicyclo[2.2.2]octan-6-one

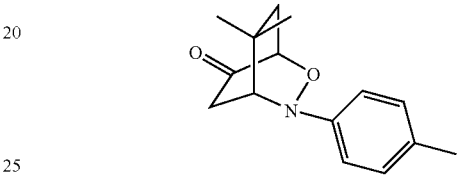

Purification by flash column chromatography with elution by (1:9 EtOAc:Hexane) provided as a yellowish crystal (46% yield, 98% ee); TLC $R_f$ 0.5 (EtOAc/Hexane 1:5); $[\alpha]_D^{27}$ +44.4° (c=1.32, CHCl$_3$); FTIR (CD$_3$Cl) $\upsilon_{max}$ 2961, 1742, 1506, 1028, 994, 817 cm$^{-1}$; $^1$H NMR (400 MHz, CD$_3$Cl) δ 7.10 (d, J=8.1 Hz, 2H), 6.98 (d, J=8.5 Hz, 2H), 4.14-4.17 (m, 1H), 3.42-3.45 (m, 1H), 2.71 (dd, J=18.7 Hz, J=2.7 Hz, 1H) 2.45 (dd, J=18.7 Hz, J=3.0 Hz, 1H) 2.30 (dd, J=14.4 Hz, J=4.0 Hz, 1H), 2.29 (s, 3H), 1.79 (dd, J=14.5 Hz, J=1.8Hz, 1H) 1.47 (s, 3H), 1.07 (s, 3H); $^{13}$C NMR (100 MHz, CD$_3$Cl) δ 208.3, 147.6, 132.0, 129.4, 116.8, 78.2, 68.6, 39.9, 34.7, 33.1, 28.6, 27.3, 20.6; C$_{15}$H$_{20}$NO$_2$ (M+H)$^+$: 246.2. Found: 246.1. Enantiometric excess was determined by HPLC with Chiralcel OD-H column×2 (99:1 hexane:2-propanol), 0.5 mL/min; major enantiomer t$_r$=38 3 min, minor enantiomer t$_r$=40.7 min.

Example 8f 3-(3,5-Dimethyl-phenyl)-8,8-dimethyl-2-oxa-3-aza-bicyclo[2.2.2]octan-6-one

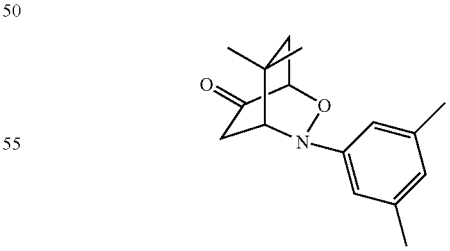

Purification by flash column chromatography with elution by (1:9 EtOAc:Hexane) provided as a yellowish crystal (52% yield, 98% ee); TLC $R_f$ 0.5 (EtOAc/Hexane 1:5); $[\alpha]_D^{27}$ +70.8° (c=0.67, CHCl$_3$); FTIR (CD$_3$Cl) $\upsilon_{max}$ 2961, 2921, 2870, 1742, 1595, 1471, 1028, 1006 cm$^{-1}$; $^1$H NMR (400 MHz, CD$_3$Cl) δ 6.70 (s, 2H), 6.64 (s, 1H), 4.14-4.17 (m, 1H), 3.47-3.51 (m, 1H), 2.72 (dd, J=18.7 Hz, J=2.7 Hz, 1H) 2.47

(dd, J=18.7 Hz, J=3.0 Hz, 1H) 2.29 (dd, J=14.4 Hz, J=3.9 Hz, 1H), 2.29 (s, 6H), 1.79 (dd, J=14.5 Hz, J=2.0 Hz, 1H) 1.46 (s, 3H), 1.07 (s, 3H); $^{13}$C NMR (100 MHz, CD$_3$Cl) δ 208.4, 150.0, 138.5, 124.2, 114.3, 78.2, 68.2, 39.9, 35.0, 33.1, 28.6, 27.3, 21.5; C$_{16}$H$_{22}$NO$_2$ (M+H)$^+$: 260.2. Found: 260.2. Enantiometric excess was determined by HPLC with Chiralcel AD-H column (97.5:2.5 hexane:2-propanol), 0.4 mL/min; major enantiomer t$_r$=13.7 min, minor enantiomer t$_r$=12.8 min.

Having thus described in detail various embodiments of the present invention, it is to be understood that the invention defined by the above paragraphs is not to be limited to particular details set forth in the above description as many apparent variations thereof are possible without departing from the spirit and scope of the present invention.

Example 8g 3-(4-Bromo-phenyl)-8,8-dimethyl-2-oxa-3-aza-bicyclo[2.2.2]octan-6-one

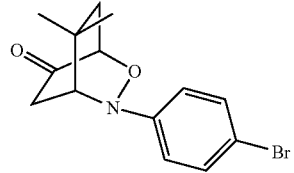

Solvent system was changed to CH$_2$Cl$_2$/MeCN 1:1 (6 mL) was used instead of use of CH$_2$Cl$_2$. Purification by flash column chromatography with elution by CH$_2$Cl$_2$ provided as a yellowish crystal (50% yield, 99% ee); TLC R$_f$ 0.6 (CH$_2$Cl$_2$); [α]$_D^{2727}$+68.1° (c=2.17, CHCl$_3$); FTIR (CD$_3$Cl) υ$_{max}$ 2962, 2871, 1742, 1587, 1485, 1436, 1028, 825 cm$^{-1}$; $^1$H NMR (400 MHz, CD$_3$Cl) δ 7.33 (d, J=8.9 Hz, 2H), 6.90 (d, J=8.9 Hz, 2H), 4.10-4.12 (m, 1H), 3.40-3.42 (m, 1H), 2.57 (dd, J=18.7 Hz, J=2.7 Hz, 1H) 2.42 (dd, J=18.7 Hz, J=2.9 Hz, 1H) 2.21 (dd, J=14.6 Hz, J=3.9 Hz, 1H) 1.73 (dd, J=14.5 Hz, J=2.3 Hz, 1H) 1.37 (s, 3H), 1.01 (s, 3H); $^{13}$C NMR (100 MHz, CD$_3$Cl) δ 207.4, 149.1, 131.8, 118.2, 114.8, 78.3, 68.3, 39.7, 35.0, 33.1, 28.6, 27.2; MS (CI) Exact Mass Calcd for C$_{14}$H$_{17}$BrNO$_2$ (M+H)$^+$: 310.0. Found: 310.0. Enantiometric excess was determined by HPLC with Chiralcel AD-H column (98:2 hexane:2-propanol), 1.0 mL/min; major enantiomer t$_r$=11.3 min, minor enantiomer t$_r$=15.3 min.

Example 8h

7-Phenyl-6-oxa-7-aza-bicyclo[3.2.2]nonan-9-one

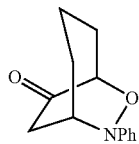

Purification by flash column chromatography with elution by (1:1 Hexane: CH$_2$Cl$_2$) provided as a yellowish oil (51% yield, 99% ee); TLC R$_f$ 0.7 (Hexane/CH$_2$Cl$_2$, 1:19); [α]$_D^{29}$-186.5° (c=1.12, CHCl$_3$); FTIR (CD$_3$Cl) υ$_{max}$ 2946, 1736, 1597, 1489, 1204, 1102, 1038, 734 cm$^{-1}$; $^1$H NMR (500 MHz, CD$_3$Cl) δ 7.31 (t, J=7.4 Hz, 2H), 7.04 (d, J=8.8 Hz, 2H), 6.92 (t, J=7.4 Hz, 1H) 4.60 (br d, J=5.8 Hz, 1H), 4.36-4.39 (m, 1H), 2.98 (dd, J=18.1 Hz, J=5.5 Hz, 1H), 2.43 (dd, J=18.1 Hz, J=2.1 Hz, 1H) 2.07-2.16 (m, 3H), 1.86-1.96 (m, 1H), 1.42-1.56 (m, 1H); $^{13}$C NMR (100 MHz, CD$_3$Cl) δ 207.5, 150.0, 129.0, 121.0, 114.7, 83.6, 56.9, 38.8, 30.9, 29.7, 18.9; MS (CI) Exact Mass Calcd for C$_{13}$H$_{15}$NO$_2$ (M+H)$^+$: 218.1. Found: 218.1. Enantiometric excess was determined by HPLC with Chiralcel AD-H column (90:10 hexane:2-propanol), 1.0 mL/min; major enantiomer t$_r$=8.5 min, minor enantiomer t$_r$=6.9 min.

What is claimed is:

1. A process of making an enantioenriched α-aminooxyketone comprising reacting a ketone of formula (II):

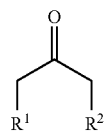

(II)

with a nitroso compound of formula (IIIa) or (IIIb):

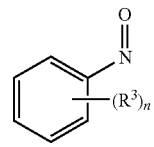

(IIIa)

(IIIb)

in the presence of a solvent and a catalyst of formula (IVa):

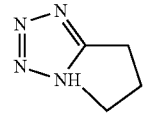

(IVa)

wherein:
R$^1$ and R$^2$ independently represent either hydrogen; a substituted or unsubstituted alkyl group; a substituted or unsubstituted alkoxy group; a substituted or unsubstituted alkoxycarbonyl group; a substituted or unsubstituted aryl group; or
R$^1$ and R$^2$ together form a cycloalkyl ring;
R$^3$ is each independently selected from the group consisting of:
hydrogen, halogen, —OR$^5$, —OC(O)R$^5$, —CN, —C(O)R$^5$, —CO$_2$R$^5$, —C(O)NR$^5$R$^{5'}$, —NO$_2$, —NR$^5$R$^{5'}$, —NRC(O)R$^5$, —NR$^5$CO$_2$R$^5$, —NR$^5$S(O)$_2$R$^{5'}$, —SR$^5$, —S(O)R$^5$, —S(O)$_2$R$^5$, —S(O)$_2$NR$^5$R$^{5'}$, C$_{1-8}$ alkyl, C$_{2-8}$ alkenyl, C$_{2-8}$ alkynyl, C$_{3-8}$ cycloalkyl, C$_{6-10}$ aryl, 5- to 10-membered heteroaryl, and 3- to 10-membered heterocyclyl; wherein each R$^5$ and R$^{5'}$ may be independently selected from the group consisting of hydrogen, C$_{1-8}$ alkyl, C$_{2-8}$ alkenyl, C$_{2-8}$ alkynyl, $C_{3-8}$ cycloalkyl, $C_{6-10}$ aryl, 5- to 10-membered heteroaryl, and 3- to 10-membered heterocyclyl;

n is an integer from 0-5;

$R^4$ is substituted or unsubstituted alkyl;

the configuration of the stereogenic carbon alpha to the nitrogen on the pyrolidine ring is the (L) or optionally (D) configuration.

2. The process of claim 1 wherein:

$R^1$ and $R^2$ independently represent either hydrogen; a substituted or unsubstituted $C_1$-$C_8$ alkyl group; a substituted or unsubstituted $C_1$-$C_8$ alkoxy group; a substituted or unsubstituted $C_1$-$C_8$ alkoxycarbonyl group; a substituted or unsubstituted aryl group, wherein the groups when substituted are substituted by the group consisting of hydrogen, halogen, —$OR^4$, —$OC(O)R^4$, —CN, —$C(O)R^4$, —$CO_2R^4$, —$C(O)NR^4R^5$, —$NO_2$, —$NR^4R^5$, —$NRC(O)R^4$, —$NR^4CO_2R^5$, —$NR^4S(O)_2R^5$, —$SR^4$, —$S(O)R^4$, —$S(O)_2R^4$, —$S(O)_2NR^4R^5$, $C_{1-8}$ alkyl, $C_{3-8}$ cycloalkyl, $C_{6-10}$ aryl, 5- to 10-membered heteroaryl, and 3- to 10-membered heterocyclyl; or $R^1$ and $R^2$ together form a $C_3$-$C_8$ cycloalkyl ring;

$R^3$ is each independently selected from the group consisting of:

hydrogen, halogen, —$OR^5$, —$OC(O)R^5$, —CN, —$C(O)R^5$, —$CO_2R^5$, —$C(O)NR^5R^{5'}$, —$NO_2$, —$NR^5R^{5'}$, —$NRC(O)R^5$, —$NR^5CO_2R^{5'}$, —$NR^5S(O)_2R^{5'}$, —$SR^5$, —$S(O)R^5$, —$S(O)_2R^5$, —$S(O)_2NR^5R^{5'}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl; wherein each $R^5$ and $R^{5'}$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

$R^4$ is a substituted or unsubstituted $C_1$-$C_8$ alkyl, wherein when substituted are substituted by the group consisting of halogen, —$OR^5$, —$OC(O)R^5$, —CN, —$C(O)R^5$, —$CO_2R^5$, —$C(O)NR^5R^{5'}$, —$NO_2$, —$NR^5R^{5'}$, —$NRC(O)R^5$, —$NR^5CO_2R^{5'}$, —$NR^5S(O)_2R^{5'}$, —$SR^5$, —$S(O)R^5$, —$S(O)_2R^5$, —$S(O)_2NR^5R^{5'}$, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl; wherein each $R^5$ and $R^{5'}$ may be independently selected from the group consisting of hydrogen, $C_{1-8}$ alkyl, $C_{2-8}$ alkenyl, $C_{2-8}$ alkynyl, $C_{3-8}$ cycloalkyl, $C_{6-10}$ aryl, 5- to 10-membered heteroaryl, and 3- to 10-membered heterocyclyl;

n is an interger from 0-3; and the configuration of the stereogenic carbone alpha to the nitrogen on the pyrolidine ring is the (L) or optionally (D) configuration.

3. The process of claim 1 wherein the enantioselectivity is greater than 99% enantiomeric excess (ee).

4. The process of claim 1 wherein the catalyst has the following structure:

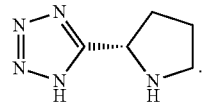

* * * * *

UNITED STATES PATENT AND TRADEMARK OFFICE
CERTIFICATE OF CORRECTION

PATENT NO. : 8,252,941 B2
APPLICATION NO. : 12/578836
DATED : August 28, 2012
INVENTOR(S) : Norie Momiyama et al.

It is certified that error appears in the above-identified patent and that said Letters Patent is hereby corrected as shown below:

IN THE CLAIMS:

Column 48, claim 1, lines 44-48:
Structure for formula IVa should be canceled and the following should be inserted:

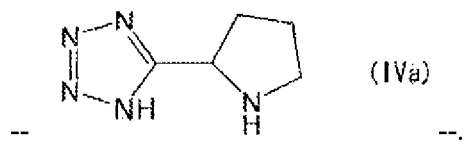

Column 50, line 19, (Claim 2, line 44), the term "carbone" should read --carbon--.

Signed and Sealed this
Twentieth Day of November, 2012

David J. Kappos
*Director of the United States Patent and Trademark Office*